(12) United States Patent
Hamers et al.

(10) Patent No.: US 7,655,759 B2
(45) Date of Patent: Feb. 2, 2010

(54) RECOMBINANT BIVALENT MONOSPECIFIC IMMUNOGLOBULIN HAVING AT LEAST TWO VARIABLE FRAGMENTS OF HEAVY CHAINS OF AN IMMUNOGLOBULIN DEVOID OF LIGHT CHAINS

(75) Inventors: Raymond Hamers, Sint-Genesius-Rode (BE); Serge Muyldermans, Sint-Genesius-Rode (BE)

(73) Assignee: Vrije Universiteit Brussel, Brussels (BE)

( * ) Notice: Subject to any disclaimer, the term of this patent is extended or adjusted under 35 U.S.C. 154(b) by 0 days.

(21) Appl. No.: 10/154,971

(22) Filed: May 28, 2002

(65) Prior Publication Data

US 2003/0088074 A1 May 8, 2003

Related U.S. Application Data

(63) Continuation of application No. 08/945,244, filed as application No. PCT/EP96/01725 on Apr. 25, 1996, now abandoned.

(30) Foreign Application Priority Data

Apr. 25, 1995 (GB) ............................... 95400932.0

(51) Int. Cl.
 *C07K 16/00* (2006.01)
(52) U.S. Cl. .................................. 530/387.3
(58) Field of Classification Search ............. 530/387.1, 530/387.3, 388.85; 424/130.1, 133.1
 See application file for complete search history.

(56) References Cited

U.S. PATENT DOCUMENTS

| | | | |
|---|---|---|---|
| 4,689,299 A | | 8/1987 | Insel et al. |
| 5,124,249 A | | 6/1992 | Khan et al. |
| 5,316,911 A | | 5/1994 | Baek et al. |
| 5,719,267 A | * | 2/1998 | Carroll et al. ............ 530/387.1 |
| 5,989,830 A | * | 11/1999 | Davis et al. ................... 435/7.1 |
| 6,005,079 A | | 12/1999 | Casterman et al. |
| 6,103,521 A | * | 8/2000 | Capon et al. ................. 435/325 |
| 6,165,745 A | * | 12/2000 | Ward et al. ................. 435/69.1 |
| 6,225,447 B1 | * | 5/2001 | Winter et al. ............. 530/387.3 |
| 6,365,158 B1 | * | 4/2002 | Williams et al. ......... 424/190.1 |
| 6,517,829 B1 | * | 2/2003 | Frenken et al. ........... 424/93.21 |
| 6,610,472 B1 | * | 8/2003 | Zhu et al. ....................... 435/5 |
| 2004/0253638 A1 | * | 12/2004 | Casterman et al. ........... 435/7.1 |

FOREIGN PATENT DOCUMENTS

| WO | WO 93 01288 A | 1/1993 |
|---|---|---|
| WO | WO 94 04678 A | 3/1994 |
| WO | WO 94 25591 | 11/1994 |

OTHER PUBLICATIONS

Oguma et al (Infection and Immunity 38:14-20, 1982).*
Els Conrath et al. (J. Biol. Chem. Mar. 9, 2001; 276 (10): 7346-7350).*
Mallender et al. (J. Biol. Chem. Jan. 7, 1994; 269 (1): 199-206).*
Arbabi Ghahroudi et al. (FEBS Lett. 1997; 414: 521-526).*
Mullinax et al., "Identification of Human Antibody Fragment Clines Specific For Tetanus Toxoid In A Bacteriophage Lambda Immunoexpression", Proceedings of the National Academy of Sciences of the USA, vol. 87, No. 20, pp. 8095-8099, Oct. 1990.
Muyldermans et al., "Sequence and Structure Of Vh Domain From Naturally Occurring Camel Heavy Chain Immunoglobulins Lacking Light Chains", Protein Engineering, vol. 7, No. 9, pp. 1129-1135, (1994).
Davies et al., "Camelising Human Antibody Fragements: NMR Studies on VH Domains", FEBS Letters, Vo. 339, No. 3, pp. 285-290, (1994).
Paul-Murphy et al., "Immune Response Of The Llama (Lama Glama) to Tetanus Toxoid Vaccination", American Journal Of Veterinary Research, Vo. 50, No. 8, pp. 1279-1281, (Aug. 1989).
Davies et al., "Antibody VH Domains As Small Recognition Units", Bio/Technology, vol. 13, No. 5, pp. 475-479, (May 1995).
Cruse et al., Illustrated Dictionary Of Immunology, CRC Press, pp. 38 and 143-144.
Hamers-Casterman et al., Nature 363, pp. 446-448, (1993).
Panka et al., Proc. Natl. Acad. Sci. USA 85, pp. 3080-3084, (1988).
Rudikoff et al., Proc. Natl. Acad. Sci. USA. 79, pp. 1979-1983, (1982).
Amit et al., Science 233, pp. 747-753, (1986).
Borrebaeck et al., (1992) *Bio/Technology* 10, 697-698.
Casali et al., (1989) *Annu. Rev. Immunol.* 7, 513-535.
Friguet et al., (1983) *J. Immunol. Meth.* 60, 351-358.
Friguet et al., (1990) In: Protein Structure. A practical approach (Ed. T.E. Creighton) IRL Press, p. 287-310.
Glockshuber et al., (1990) *Biochemistry* 29, 1362-1367.
Hoogenboom et al., (1991) *Nucl. Acids Res.* 19, 4133-4137.
Johnson, W.C., (1990) *Proteins: Structure, Func. & Genetics* 7, 205-214.
Marks et al., (1991) *J. Mol. Biol.* 222, 581-597.
Montecucco & Schiavo, (1993) *TIBS* 18, 324-329.
Persson et al., (1991) *Proc. Natl. Acad. Sci. USA* 88, 2432-2439.
Simpson et al., (1990) *J. Pharmacol. & Exp. Therap.* 254(1): 98-103.
Skerra & Pluckthun, (1988) *Science* 240, 1038-1040.
Arturson, G. et al., "Intravascular Persistence and Renal Clearance of Dextran of Different Molecular Sizes in Normal Children," *Arch. Dis. Childh.* 1966; 41:168-171.
Knauf, M. J. et al., "Relationship of Effective Molecular Size to Systemic Clearance in Rats of Recombinant Interleukin-2 Chemically Modified with Water-soluble Polymers," *The Journal of Biological Chemistry* 1988; 263(29):15064-15070.

* cited by examiner

*Primary Examiner*—Stephen L Rawlings
(74) *Attorney, Agent, or Firm*—Wolf, Greenfield & Sacks, P.C.

(57) ABSTRACT

The present invention relates to fragments, especially variable fragments of immunoglobulins which are by nature devoid of light chains, these fragments being nevertheless capable of exhibiting a recognition and binding activity toward specific antigens. The present invention further relates to the use of such immunoglobulin fragments formed of at least one heavy chain variable fragment or derived therefrom, for therapeutic or veterinary purposes and especially for passive immunotherapy or serotherapy.

18 Claims, 22 Drawing Sheets

```
Pel B leader signal - - - I  Q   V   Q   L    Q   (VH cloning
GCG GCC CAG CCG GCC ATG GCC CAG CTG CAG CTG CAG GAC CTC
        Sfi I                                Pst I site)           V   T   V   S   S            I- - - - - - -
GAG GAT CCG GTC ACC GTC TCC AGC GGC CGC TAC CCG TAC GAC
            Bst EII         Not I decaptide tag - - - - I                     I -- genIIIp
GTT CCG GAC TAC GGT TCC GGC CGA GCA TAG ACT GTT
                        Eag I        amber
``` pHEN4-αTT1

```
           10        20        30        40        50        60
            |         |         |         |         |         |
        GAGGTGCAGCTGCAGGCGTCTGGGGGAGGCTCGGTGCAGGCTGGAGGGTCTCTGAGACTC
        GluValGlnLeuGlnAlaSerGlyGlyGlySerValGlnAlaGlyGlySerLeuArgLeu
                                        ===

70        80        90       100       110       120
            |         |         |         |         |         |
        TCCTGTGCGGCCTCTGGGGGACAGACCTTCGATAGTTATGCCATGGCCTGGTTCCGCCAG
        SerCysAlaAlaSerGlyGlyGlnThrPheAspSerTyrAlaMETAlaTrpPheArgGln
                                                      ===       ===

130       140       150       160       170       180
            |         |         |         |         |         |
        GCTCCAGGGAAGGAGTGCGAATTGGTCTCGAGTATTATTGGTGATGATAACAGAAACTAT
        AlaProGlyLysGluCysGluLeuValSerSerIleIleGlyAspAspAsnArgAsnTyr
                        ===

190       200       210       220       230       240
            |         |         |         |         |         |
        GCCGACTCCGTGAAAGGCCGATTCACCATCTCCCGAGACAACGCCAAGAACACGGTATAT
        AlaAspSerValLysGlyArgPheThrIleSerArgAspAsnAlaLysAsnThrValTyr 250       260       270       280       290       300
            |         |         |         |         |         |
        CTGCAAATGGACCGTCTGAATCCTGAGGACACGGCCGTGTATTACTGTGCGCAATTGGGT
        LeuGlnMETAspArgLeuAsnProGluAspThrAlaValTyrTyrCysAlaGlnLeuGly 310       320       330       340       350
            |         |         |         |         |
        AGTGCCCGGTCGGCTATGTACTGTGCGGGCCAGGGGACCCAGGTCACCGTCTCCTCA
        SerAlaArgSerAlaMETTyrCysAlaGlyGlnGlyThrGlnValThrValSerSer
```

FIGURE 4A pHEN4-αTT2

```
            10        20        30        40        50        60
             |         |         |         |         |         |
        GAGGTGCAGCTGCAGGCGTCTGGAGGAGGCTCGGTGCAGGCTGGAGGGTCTCTGAGGCTC

GluValGlnLeuGlnAlaSerGlyGlyGlySerValGlnAlaGlyGlySerLeuArgLeu
```

```
            70        80        90        100       110       120
             |         |         |         |         |         |
        TCTTGTACAGCCGCTAATTACGCCTTTGATTCCAAGACCGTGGGCTGGTTCCGCCAGGTT

SerCysThrAlaAlaAsnTyrAlaPheAspSerLysThrValGlyTrpPheArgGlnVal
```

```
            130       140       150       160       170       180
             |         |         |         |         |         |
        CCAGGAAAGGAGCGCGAGGGGGTCGCGGGTATCAGTAGTGGTGGCAGTACCACAGCCTAT

ProGlyLysGluArgGluGlyValAlaGlyIleSerSerGlyGlySerThrThrAlaTyr
```

```
            190       200       210       220       230       240
             |         |         |         |         |         |
        TCCGACTCCGTGAAGGGCCGATACACCGTCTCCCTTGAGAACGCCAAGAACACTGTGTAT

SerAspSerValLysGlyArgTyrThrValSerLeuGluAsnAlaLysAsnThrValTyr
```

```
            250       260       270       280       290       300
             |         |         |         |         |         |
        CTACTGATAGACAACCTACAACCTGAAGACACTGCCATATACTACTGCGCAGGAGTGAGC

LeuLeuIleAspAsnLeuGlnProGluAspThrAlaIleTyrTyrCysAlaGlyValSer
```

```
            310       320       330       340       350       360
             |         |         |         |         |         |
        GGTTGGCGAGGGCGGCAGTGGCTGCTACTGGCAGAGACCTATCGGTTCTGGGGCCAGGGG

GlyTrpArgGlyArgGlnTrpLeuLeuLeuAlaGluThrTyrArgPheTrpGlyGlnGly
```

```
            370       380
             |         |
        ACTCAGGTCACCGTCTCCTCA

ThrGlnValThrValSerSer
```

FIGURE 4B

FIG_9

```
GAG GTC CAG CTG CAG GCG TCT GGA GGA GGC TCG GTG CAG GCT GGA CAG    48
Glu Val Gln Leu Gln Ala Ser Gly Gly Gly Ser Val Gln Ala Gly Gln
                                        11

TCT CTG AGA CTC TCC TGT GCG ACC TCT GGA GCC ACC TCC AGT AGC AAC    96
Ser Leu Arg Leu Ser Cys Ala Thr Ser Gly Ala Thr Ser Ser Asn Ser

TGC ATG GGC  TGG TTC CGC CAG GCT CCA GGG AAG GAG CGC GAG GGG GTC   144
Cys MET Gly  Trp Phe Arg Gln Ala Pro Gly Lys Glu Arg Glu Gly Val
             37                      44  45      47
CDR1

GCA GTT ATT GAT ACT GGT AGA GGG AAT ACA GCC TAT GCC GAC TCC GTG   192
Ala Val Ile Asp Thr Gly Arg Gly Asn Thr Ala Tyr Ala Asp Ser Val
                                 CDR2

CAG GGC  CGA TTG ACC ATC TCC TTA GAC AAC GCC AAG AAC ACG CTA TAT   240
Gln Gly  Arg Leu Thr Ile Ser Leu Asp Asn Ala Lys Asn Thr Leu Tyr

CTG CAA ATG AAC AGC CTG AAA CCT GAG GAC ACT GCC ATG TAC TAC TGT   288
Leu Gln MET Asn Ser Leu Lys Pro Glu Asp Thr Ala MET Tyr Tyr Cys

GCA GCA GAT ACA TCC ACT TGG TAT CGT GGT TAC TGC GGA ACA AAT CCA   336
Ala Ala Asp Thr Ser Thr Trp Tyr Arg Gly Tyr Cys Gly Thr Asn Pro
                                CDR3

AAT TAC TTT TCG TAC TGG GGC CAG GGG ACC CAG GTC ACC GTC TCC TCA   384
Asn Tyr Phe Ser Tyr Trp Gly Gln Gly Thr Gln Val Thr Val Ser Ser
```

FIGURE 11

```
GAT GTG CAG CTG CAG GCG TCT GGA GGA GGC TCG GTG CAG GCT GGA GGG      48
Asp Val Gln Leu Gln Ala Ser Gly Gly Gly Ser Val Gln Ala Gly Gly
                                     11

TCT CTG AGA CTC TCC TGT GCA GCC TCT GGA TAC ACC ATC GGT CCC TAC      96
Ser Leu Arg Leu Ser Cys Ala Ala Ser Gly Tyr Thr Ile Gly Pro Tyr

TGT ATG GGG  TGG TTC CGC CAG GCC CCA GGG AAG GAG CGT GAG GGG GTC    144
Cys MET Gly  Trp Phe Arg Gln Ala Pro Gly Lys Glu Arg Glu Gly Val
             37                          44  45     47
CDR1

GCA GCA ATT AAT ATG GGT GGT GGT ATC ACC TAC TAC GCC GAC TCC GTG    192
Ala Ala Ile Asn MET Gly Gly Gly Ile Thr Tyr Tyr Ala Asp Ser Val
                             CDR2

AAG GGC  CGA TTC ACC ATC TCC CAA GAC AAC GCC AAG AAC ACG GTG TAT   240
Lys Gly  Arg Phe Thr Ile Ser Gln Asp Asn Ala Lys Asn Thr Val Tyr

CTG CTC ATG AAC AGC CTA GAA CCT GAG GAC ACG GCC ATC TAT TAC TGT    288
Leu Leu MET Asn Ser Leu Glu Pro Glu Asp Thr Ala Ile Tyr Tyr Cys

GCG GCA GAT TCG ACC ATC TAC GCT AGT TAT TAT GAA TGT GGT CAC GGT    336
Ala Ala Asp Ser Thr Ile Tyr Ala Ser Tyr Tyr Glu Cys Gly His Gly
            CDR3

CTT TCC ACG GGA GGA TAT GGG TAT GAC TCC  TGG GGC CAG GGG ACC CAG   384
Leu Ser Thr Gly Gly Tyr Gly Tyr Asp Ser  Trp Gly Gln Gly Thr Gln

GTC ACC GTC TCC TCA  A                                              400
Val Thr Val Ser Ser
```

FIGURE 12

```
GAT GTG CAG CTG CAG GCG TCT GGA GGA GGC TCG GTG CAG GCT GGA GGG        48
Asp Val Gln Leu Gln Ala Ser Gly Gly Gly Ser Val Gln Ala Gly Gly
→α LY83                                    11

TCT CTG AGA CTC TCC TGT GCA GCC TCT GGA TAC ACC ATC GGT CCC TAC        96
Ser Leu Arg Leu Ser Cys Ala Ala Ser Gly Tyr Thr Ile Gly Pro Tyr

TGT ATG GGG TGG TTC CGC CAG GCC CCA GGG AAG GAG CGT GAG GGG GTC       144
Cys MET Gly Trp Phe Arg Gln Ala Pro Gly Lys Glu Arg Glu Gly Val
CDR1                                              44  45      47
     37

GCA GCA ATT AAT ATG GGT GGT GGT ATC ACC TAC TAC GCC GAC TCC GTG       192
Ala Ala Ile Asn MET Gly Gly Gly Ile Thr Tyr Tyr Ala Asp Ser Val
                                        CDR2

AAG GGC CGA TTC ACC ATC TCC CAA GAC AAC GCC AAG AAC ACG GTG TAT       240
Lys Gly Arg Phe Thr Ile Ser Gln Asp Asn Ala Lys Asn Thr Val Tyr

CTG CTC ATG AAC AGC CTA GAA CCT GAG GAC ACG GCC ATC TAT TAC TGT       288
Leu Leu MET Asn Ser Leu Glu Pro Glu Asp Thr Ala Ile Tyr Tyr Cys
```

FIGURE 15A

```
GAT GTG CAG CTG CAG GCG TCT GGA GGA GGC TCG GTG CAG GCT GGA GGG      48
Asp Val Gln Leu Gln Ala Ser Gly Gly Gly Ser Val Gln Ala Gly Gly
└→αLYS3                                   11

TCT CTG AGA CTC TCC TGT GCA GCC TCT GGA TAC ACC ATC GGT CCC TAC      96
Ser Leu Arg Leu Ser Cys Ala Ala Ser Gly Tyr Thr Ile Gly │Pro Tyr│

TGT ATG GGG TGG TTC CGC CAG GCC CCA GGG AAG GAG CGT GAG GGG GTC     144
│Cys MET Gly│ Trp Phe Arg Gln Ala Pro Gly Lys Glu Arg Glu Gly Val
 CDR1
      37                                        44   45          47

GCA GCA ATT AAT ATG GGT GGT ATC ACC TAC TAC GCC GAC TCC GTG         192
Ala │Ala Ile Asn MET Gly Gly Gly Ile Thr Tyr Tyr Ala Asp Ser Val│
                                  CDR2

AAG GGC CGA TTC ACC ATC TCC CAA GAC AAC GCC AAG AAC ACG GTG TAT     240
│Lys Gly│ Arg Phe Thr Ile Ser Gln Asp Asn Ala Lys Asn Thr Val Tyr

CTG CTC ATG AAC AGC CTA GAA CCT GAG GAC ACG GCC ATC TAT TAC TGT     288
Leu Leu MET Asn Ser Leu Glu Pro Glu Asp Thr Ala Ile Tyr Tyr Cys
```

FIGURE 16A

```
GCG GCA GAT TCG ACC ATC TAC GCT AGT TAT TAT GAA TGT GGT CAC GGT    336
Ala Ala Asp Ser Thr Ile Tyr Ala Ser Tyr Tyr Glu Cys Gly His Gly
            └─────────────────── CDR3 ───────────────────┘

CTT TCC ACG GGA GGA TAT GGG TAT GAC TCC TGG GGC CAG GGG ACC CAG    384
Leu Ser Thr Gly Gly Tyr Gly Tyr Asp Ser Trp Gly Gln Gly Thr Gln

GTC ACC GTC TCC TCA GAA CCC AAG ATA CCA CAA CCA CAA CCA AAA CCA    432
Val Thr Val Ser Ser Glu Pro Lys Ile Pro Gln Pro Gln Pro Lys Pro
      αLYS3 ──┘ └── HINGE        LINKER

CAA CCA CAA CCA CAA CCA CAA CCA AAA CCA CAA CCA AAA CCT GAA CCC    480
Gln Pro Gln Pro Gln Pro Gln Pro Lys Pro Gln Pro Lys Pro Glu Pro
                                              LINKER HINGE ──┘

ATG GCA GAG GTC CAG CTG CAG CTG CAG GCG TCT GGA GGC TCG GTG CAG GCT    528
MET Ala Glu Val Gln Leu Gln Leu Gln Ala Ser Gly Gly Ser Val Gln Ala
NcoI                                                      11
     αLYS2

GGA CAG TCT CTG AGA CTC TCC TGT GCG ACC TCT GGA GCC ACC TCC AGT    576
Gly Gln Ser Leu Arg Leu Ser Cys Ala Thr Ser Gly Ala Thr Ser Ser
```

FIGURE 15B

```
AGC AAC TGC ATG GGC    TGG TTC CGC CAG GCT CCA GGG AAG GAG CGC GAG      624
 Ser Asn Cys MET Gly   Trp Phe Arg Gln Ala Pro Gly Lys Glu Arg Glu
       CDR1                      37                          44   45

GGG GTC GCA GTT ATT GAT ACT GGT AGA GGG AAT ACA GCC TAT GCC GAC          672
Gly Val Ala Val Ile Asp Thr Gly Arg Gly Asn Thr Ala Tyr Ala Asp
             47                                      CDR2'

TCC GTG CAG GGC    CGA TTG ACC ATC TCC TTA GAC AAC GCC AAG AAC ACG      720
Ser Val Gln Gly    Arg Leu Thr Ile Ser Leu Asp Asn Ala Lys Asn Thr

CTA TAT CTG CAA ATG AAC AGC CTG AAA CCT GAG GAC ACT GCC ATG TAC          768
Leu Tyr Leu Gln MET Asn Ser Leu Lys Pro Glu Asp Thr Ala MET Tyr

TAC TGT GCA GCA GAT ACA TCC ACT TGG TAT CGT GGT TAC TGC GGA ACA          816
Tyr Cys Ala Ala Asp Thr Ser Thr Trp Tyr Arg Gly Tyr Cys Gly Thr
                                              CDR3

AAT CCA AAT TAC TTT TCG TAC    TGG GGC CAG GGG ACC CAG GTC ACC GTC      864
Asn Pro Asn Tyr Phe Ser Tyr    Trp Gly Gln Gly Thr Gln Val Thr Val

TCC AGC GGC CGC TAC GAC GTT CCG GAC TAC GGT TCC GGC CGA GCA TAG         912
    Not I    Gly Arg Tyr Asp Val Pro Asp Tyr Gly Ser Gly Arg Ala  ---
Ser Ser
 αLYS2                              TAG

FIGURE 16C
```

RECOMBINANT BIVALENT MONOSPECIFIC IMMUNOGLOBULIN HAVING AT LEAST TWO VARIABLE FRAGMENTS OF HEAVY CHAINS OF AN IMMUNOGLOBULIN DEVOID OF LIGHT CHAINS

This application is a continuation of Ser. No. 08/945,244 filed Jan. 16, 1998, now abandoned. which is a national stage of PCT/EP96/01725 filed Apr. 25, 1996.

The present invention relates to fragments, especially variable fragments of immunoglobulins which are by nature devoid of light chains these fragments being nevertheless capable of exhibiting a recognition and binding activity toward specific antigens. These fragments of immunoglobulins can for example be obtained by the expression in host cells for example in prokaryotic cells or eukaryotic cells of nucleotide sequences obtained from animals naturally expressing so-called "two-chain immunoglobulins", for instance from animals of the camelid family.

The present invention further relates to the use of such immunoglobulin fragments formed of at least one heavy chain variable fragment or derived therefrom, for therapeutic or veterinary purposes and especially for passive immunotherapy or serotherapy.

Functional immunoglobulins devoid of light polypeptide chains termed <<two-chain immunoglobulin>> or <<heavy-chain immunoglobulin>> have been obtained from animals of the family of camelids and have been described in an international patent application published under number WO 94/04678, together with two publications, especially Hamers-Casterman et at, 1993 and Muyldermans et al, 1994).

The isolation and characterization of these immunoglobulins, together with their cloning and sequencing have been described in the above referrenced documents which are incorporated by reference in the present application.

According to WO 94/04678 it has been established that different molecules can be isolated from animals which naturally produce them, which molecules have functional properties of the well known four-chain immunoglobulins these functions being in some cases related to structural elements which are distinct from those involved in the function of four-chain immunoglobulins due for instance to the absence of light chains.

These immunoglobulins having only two chains, neither correspond to fragments obtained for instance by the degradation in particular the enzymatic degradation of a natural four-chain model immunoglobulin, nor correspond to the expression in host cells, of DNA coding for the constant or the variable regions of a natural four-chain model immunoglobulin or a part of these regions, nor correspond to antibodies produced in lymphopathies for example in mice, rats or human.

The immunoglobulins devoid of light chains are such that the variable domains of their heavy chains have properties differing from those of the four-chain immunoglobulin variable heavy chain ($V_H$). For clarity reasons, this variable domain according to the invention will be called $V_{HH}$ in this text to distinguish it from the classical $V_H$ of four-chain immunoglobulins. The variable domain of a heavy-chain immunoglobulin according to the invention has no normal interaction sites with the $V_L$ or with the $C_H1$ domain which do not exist in the heavy-chain immunoglobulins. It is hence a novel fragment in many of its properties such as solubility and conformation of main chains. Indeed the $V_{HH}$ of the invention can adopt a three-dimensional organization which distinguishes from the three-dimensional organization of known four-chain immunoglobulins according to the description which is given by Chothier C. and Lesk A. M, (1987-J. Mol. Biol. 197, 901-917).

According to the results presented in patent application WO 94/04678, the antigen binding sites of the isolated immunoglobulins, naturally devoid of light chains are located on the variable region of their heavy chains. In most cases, each heavy chain variable region of these two-chain immunoglobulins can comprise an antigen binding site.

A further characteristic of these two-chain immunoglobulins is that their heavy polypeptide chains contain a variable region ($V_{HH}$) and a constant region ($C_H$) according to the definition of Roitt et al but are devoid of the first domain of the constant region is called $C_H1$.

These immunoglobulins of the type described hereabove can comprise type G immunoglobulins and especially immunoglobulins which are termed immunoglobulins of class 2 (IgG2) or immunoglobulins of class 3 (IgG3), according to the classification established in patent application WO 94/04678 or in the publication of Muyldermans et al (Protein Engineering Vol. 7, N°9, pp 1129-1135-1994).

The absence of the light chain and of the first constant domain lead to a modification of the nomenclature of the immunoglobulin fragments obtained by enzymatic digestion, according to Roitt et al.

The terms Fc and pFc on the one hand, Fc' and pFc' on the other hand corresponding respectively to the papain and pepsin digestion fragments are maintained.

The terms Fab, $F(ab)_2$, $F(ab')_2$, Fabc, Fd and fv are no longer applicable in their original sense as these fragments have either a light chain, the variable part of the light chain or the $CH_1$ domain.

The fragments obtained by papain digestion or by V8 digestion, composed of the $V_{HH}$ domain of the hinge region will be called $FV_{HH}h$ or $F(V_{HH}h)2$ depending upon whether or not they remain linked by the disulphide bonds.

The immunoglobulins referring to the hereabove given definitions can be originating from animals especially from animals of the camelid family. These heavy-chain immunoglobulins which are present in camelids are not associated with a pathological situation which would induce the production of abnormal antibodies with respect to the four-chain immunoblobulins. On the basis of a comparative study of old world camelids (*Camelus bactrianus* and *Camelus dromaderius*) and new world camelids (for example *Lama Paccos, Lama Glama*, and *Lama Vicugna*) the inventors have shown that the immunoglobulins devoid of light polypeptide chains are found in all species. Nevertheless differences may be apparent in molecular weight of these immunobglobulins depending on the animals. Especially the molecular weight of a heavy chain contained in these immunoglobulins can be from approximately 43 kd to approximately 47 kd, in particular 45 kd.

Advantageously the heavy-chain immunoglobulins. of the invention are secreted in blood of camelids.

The variable fragments of heavy chains of Immunoglobulins devoid of light chains can be prepared starting from immunoglobulins obtainable by purification from serum of camelids according to the process for the purification as described in detail in the examples of WO 94/04678. The variable fragments can also be obtained from heavy-chain immunoglobulins by digestion with papain or V8 enzymes.

These fragments can also be generated in host cells by genetic engineering or by chemical synthesis. Appropriate host cells are for instance bacteria (e.g. *E. coli*) eucaryotic cells including yeasts or animal cells including mammalian cells, or plant cells.

The observation by the inventors that Camelidae produce a substantial proportion of their functional immunoglobulins as a homodimer of heavy chains lacking the $C_H1$ domain and devoid of light chains(Hamers-Casterman et al, 1993), led to the proposal of having recourse to an immunized camel to generate and select single variable antibody fragments ($V_{HH}$) and furthermore give access to the corresponding nucleotide sequences.

Cloned camel single $V_{HH}$ fragments were displayed on bacteriophages for selection and in bacteria for the large scale production of the soluble proteins, and were shown to possess a superior solubility behaviour and affinity properties compared to the mouse or human $V_H$ equivalents (Muyldermans et al, 1994). Following this strategy, one would obtain small ligand binding molecules (MW around 16,000 D) which are not hindered by the presence of an oligopeptide linker (Borrebaeck et al. 1992) or not inactivated by the disassembly of the VH-VL complex (Glockshuber et al., 1990). The camel $V_{HH}$ fragments have the additional advantage that they are characteristic of the heavy chain antibodies which are matured in vivo in the absence of light chains.

SUMMARY OF INVENTION

The inventors have obtained evidence that variable fragments of high chains of immunoglobulins devoid of light chains can display an effective therapeutic activity when they are generated against a determined antigen.

To develop this technology of preparing and identifying useful camel $V_{HH}$ fragments, it is critical (I) that camels can be immunized with a variety of antigens, (ii) that the camel $V_{HH}$ genes can be cloned and expressed on filamenteous phages and in E. coli for easy selection with the immobilized antigen by panning, (iii) that the expressed camel $V_{HH}$'s are properly folded, and (iv) that they have good solubility properties and possess high affinities and specificities towards their antigen.

Camel $V_{HH}$ genes derived from the heavy chain immunoglobins lacking the light chains were previously cloned and analysed (Muyldermans et al., 1994). A comparison of the amino acid sequences of these camel $V_{HH}$ clones clearly showed that the key features for preserving the characteristic immunoglobulin fold are all present. The specific amino acid replacements observed in the camel $V_{HH}$ clones could correlate with the absence of the VL (variable light chains) and the functionality of the camel single $V_{HH}$ domain (Muyldermans et al., 1994).

The invention thus relates to a variable fragment ($V_{HH}$) of a heavy chain of an immunoglobulin devoid of light chains, which is encoded by a nucleotide sequence obtainable by the following process:

treating blood lymphocytes or other appropriate cells of an animal of the Camelid family previously immunized with a determined antigen, in order to give access to their mRNA, synthesizing a first strand of cDNA starting from the obtained mRNA, contacting the obtained cDNA with at least two different primer oligonucleotides in conditions allowing their hybridization to at least two complementary nucleotide sequences contained in the cDNA, said primers comprising a BACK primer (back p1) having nucleotide sequence (SEQ ID NO:1): 5'-GATGTGCAGCTGCAG-GCGTCTGG(A/G)GGAGG-3' and a FOR primer (for p1) replying to the following nucleotide sequence (SEQ ID NOS 2 & 3, respectively):

5'-CGCCATCAAGGTACCGTTGA-3' or

5'-CGCCATCAAGGTACCAGTTGA-3' amplifying the DNA fragment located between the nucleotide sequence hybridized with said primers and, recovering amplified DNA corresponding to bands of different size orders including:

a band of around 750 basepairs which is the amplified product of the variable heavy chain ($V_H$), CH1, hinge and part of CH2 region of a four-chain immunoglobin, a band of around 620 basepairs which is the amplified product of the variable heavy-chain ($V_{HH}$), long hinge, and part of the CH2 of the camel two-chain immunoglobulin IgG2, a band of around 550 basepairs which is the amplified product of the variable heavy-chain ($V_{HH}$), short hinge, and part of the CH2 of the camel two-chain immunoglobulin IgG3, purifying the two shortest bands of around 620 and 550 basepairs from agarose gel, for example by Gene Clean, recovering the amplified DNA fragments containing nucleotide sequences encoding the $V_{HH}$ fragments, digesting the amplified products with restriction enzymes having target sites within the amplified fragments and/or in the nucleotide primers, for example with PstI and BstEII, recovering the digested amplified DNA fragments, ligating the amplified DNA fragments to a phasmid vector, for example in a pHEN4 vector, in conditions allowing the expression of the amplified fragments when the obtained recombinant vector is used to transform a host cell, transforming a determined bacterial host cell for example an E. Coli cell with the obtained recombinant phasmid vector, and growing the cells on selective medium, to form a library, infecting the obtained library of recombinant host cells after culture in an appropriate selective medium, with bacteriophages, for instance M13K07 bacteriophages to obtain recombinant phagemid virions, incubating the recombinant host cells in conditions allowing secretion of recombinant phagemid virions particles containing the recombinant phasmid, for instance the pHEN4 phasmid packaged within the M13 virion.

isolating and concentrating the recombinant phagemid virions, submitting the phagemid virions to several rounds of panning with the antigen of interest previously immobilized, in conditions allowing the adsorption of the phagemid virions on the immobilized antigen, eluting the adsorbed phagemid virions, and growing them on appropriate cells, amplifying the phagemid virions by infecting the cells with helper bacteriophage, recovering the virions and testing them for their binding activity against the antigen of interest, for example by ELISA, recovering the phagemid virions having the appropriate binding activity, isolating the nucleotide sequence contained in the phasmid vector and capable of being expressed on the phagemid virions as a $V_{HH}$ aminoacid sequence having the appropriate binding activity.

In a preferred embodiment of the invention, the variable $V_{HH}$ fragments are obtainable by adding to the hereabove described amplification step of the cDNA with BACK and FOR primers (p1), a further amplification step with a BACK primer corresponding to the oligonucleotide sequence which has been described hereabove (back p1) and the FOR primer (for p2) having the following nucleotide sequence (SEQ ID NO:4): 5'-CG ACT AGT <u>GCGGCCGCG</u> TGA GGA GAC <u>GGTGAC</u> CTG-3'. Not and BstEll sites which can be used for cloning in the pHEN4 vector have been underlined. This FOR primer allows hybridization to the coden position of framework 4 (FR4) region of the $V_{HH}$ nucleotide sequences (amino acid position 113-103).

According to another variant of the process described, this additional amplification step can replace the amplification step which has been described with BACK primer and a FOR primer having respectively the following nucleotide sequences (SEQ ID NOS 1-3, respectively):

```
5'-GATGTGCAGCTGCAGGCGTCTGG(A/G)GGAGG-3'

5'-CGCCATCAAGGTACCGTTGA-3'              or

5'-CGCCATCAAGGTACCAGTTGA-3'
```

The restriction sites have been underlined.

In another embodiment of the invention the amplification step of the synthetized cDNA is performed with oligonucleotide primers including hereabove described BACK primer and FOR primer having the following sequences (SEQ ID NOS 5 & 6, respectively):

```
FOR primer 3:
5'-TGT CTT GGG TTC TGA GGA GAC GGT-3'
```

According to this latter embodiment, the $V_{HH}$ fragments of the invention are immediately and specifically amplified by a single amplification (for instance PCR reaction) step when the mixture of FOR primers is used.

These latter primers hybridize with the hinge/framework 4 and short hinge/framework 4 respectively. Each of these FOR primers allows the amplification of one IgG class according to the classification given in patent application WO 94/04678.

The variable $V_{HH}$ fragments corresponding to this definition can also be obtained from other sources of animal cells, providing that these animals are capable of naturally producing immunoglobulins devoid of light chains according to those described in the previous patent application WO 94/04678.

These variable fragments ($V_{HH}$) can also be obtained by chemical synthesis or by genetic engineering starting from DNA sequences which can be obtained by the above described process.

The variable fragment of a heavy chain of an immunoglobulin devoid of light chains according to the preceding definitions is specifically directed against an antigen against which the animal has been previously immunized, either by natural contact with this antigen or by administration of this antigen in order to generate an immune response directed against it.

The process which is proposed hereabove to prepare a nucleotide sequence coding for the variable fragments of the invention contains steps of phage display library construction which allow the selection of nucleotide sequences coding for variable fragments of heavy chains having the desired specificity.

According to one preferred embodiment of the invention, the variable fragments of a heavy chain of a immunoglobulin is obtainable from an animal having been previously immunized with a toxin, especially a toxin of a bacteria or a part of this toxin sufficient to enable the production of immunoglobulins directed against this toxin and especially immunoglobulins devoid of light chains.

According to another embodiment of the invention, the variable fragments of a heavy chain of a immunoglobulin is obtainable from an animal having been previously immunized with substances contained in venom of animals.

The antigen used for immunization of the animals is usually under a non toxic form.

The variable fragments according to the invention can be derived from immunoglobulins belonging to different classes especially belonging to IGg2 or IGg3 immunoglobulin classes, according to the classification given in patent application WO/04678.

In a preferred embodiment of the invention, the variable fragment of a heavy-chain of an immunoglobulin devoid of light chains is directed against the tetanus toxin of *Clostridium tetani* or against a fragment thereof.

The variable fragments of heavy chains of immunoglobulins devoid of light chains can be also generated against toxins or part thereof from pathogenic organisms such as bacteria and especially can be chosen among the toxins or toxoids of the following bacteria: *Clostridium*, especially *Clostridium Botulinum* or *Clostridium Perfringens*, *Staphylococcus*, *Pseudomonas*, *Pasteurella*, *Yersinia*, *Bacillus Anthracis*, *Neisseria*, *Vibrio*, especially *Vibrio cholera*, enterotoxic *E. Coli*, *Salmonella*, *Shigella*, *Listeria*.

Other antigens appropriate for the preparation of the $V_{HH}$ fragments of the invention can be obtained from the following organism: anemonies, coral, jellyfish, spiders, beas, wasps, scorpions, snakes, including those belonging to the families of Viperidae, Crotalidae, Lapidea.

According to another embodiment of the invention, the variable fragment $V_{HH}$ of a heavy chain of an immunoglobulin devoid of light chains is characterized in that it comprises the following aminoacid sequences (SEQ ID NOS 25 & 26, respectively):

(Glu/Asp)ValGlnLeuGlnAlaSerGlyGlyGlySerValGlnAla

Gly(Gly/Gln)SerLeuArgLeuSerCysAla(Ala/Thr)SerGly (CDR1)Trp(<u>Phe</u>/Tyr)ArgGlnAlaProGlyLys

<u>Glu</u>(<u>Arg</u>/Cys)<u>Glu</u>(<u>Gly</u>/Leu)Val(Ser/Ala)(CDR2)Arg(Phe/

Leu)ThrIleSer(Arg/Leu/Gln)AspAsnAlaLysAsnThr(Val/

Leu)TyrLeu(Gln/Leu)MetAsnSerLeu(Lys/Glu)ProGluAsp

ThrAla(Val/Met/Ile)TyrTyrCysAlaAla(CDR3)TrpGlyGln

GlyThrGlnValThrValSerSer or (Glu/Asp)ValGlnLeuGlnAlaSerGlyGlyGlySerValGlnAla

Gly(Gly/Gln)SerLeuArgLeuSerCysAla(Ala/Tlu)SerGly (Ala,Thr,Ser,Ser/Tyr,Thr,Ile,Gly)(CDR1)Trp(<u>Phe</u>/

Tyr)ArgGlnAlaProGlyLys<u>Glu</u>(<u>Arg</u>/Cys)<u>Glu</u>(<u>Gly</u>/Leu)Val (Ser/Ala)(CDR2)Arg(Phe/Leu)ThrIleSer(Arg/Leu/Gln)

AspAsnAlaLysAsnThr(Val/Leu)TyrLeu(Gln/Leu)MetAsn

-continued
SerLeu(Lys/Glu)ProGluAspThrAla(Val/Met/Ile)TyrTyr

CysAlaAla(CDR3)TrpGlyGlnGlyThrGlnValThrValSerSer, wherein CDR1, CDR2 and CDR3 represent variable amino acid sequences providing for the recognition of a determined epitope of the antigen used for the immunization of Camelids, CDR1, CDR2 and CDR3 sequences comprising from 5 to 25 amino acid residues preferably CDR1 contains from 7 to 12 amino acid residues, CDR2 contains from 16 to 21 amino acid residues and CDR3 contains from 7 to 25 amino acid residues.

The camel $V_{HH}$ specific amino acid residues Ser 11, Phe 37, Glu 44, Arg 45, Glu 46, Gly 47 are underlined.

One preferred variable fragment according to the invention is encoded by a nucleotide sequence present in recombinant phasmid pHEN4-αTT2(WK6) deposited at the BCCM/LMBP (Belgium) under accession number LMBP3247.

The pHEN4-αTT2 (described in FIG. 2) is a phasmid carrying a PeIB leader signal, a camel $V_{HH}$ gene of which the protein binds tetanus toxoid, a decapeptide tag (from inimunoZAP H of Stratacyte) and gene IIIp of M13 in the pUC 119 polylinker between the HindIII and EcoRI sites. This phasmid was transformed in *E. coli* WK6 cells.

A specific variable gragment according to the invention is for instance characterized in that it comprises the following αTT1 aminoacid sequence (SEQ ID NO: 7):

GluValGlnLeuGlnAlaSerGlyGlyGlySerValGlnAlaGlyGly

SerLeuArgLeuSerCysAlaAlaSerGlyGlyGlnThrPheAspSer

TyrAlaMetAlaTrpPheArgGlnAlaProGlyLysGluCysGluLeu

ValSerSerIleIleGlyAspAspAsnArgAsnTyrAlaAspSerVal

LysGlyArgPheThrIleSerArgAspAsnAlaLysAsnThrValTyr

LeuGlnMetAspArgLeuAsnProGluAspThrAlaValTyrTyrCys

AlaGlnLeuGlySerAlaArgSerAlaMetTyrCysAlaGlyGlnGly

ThrGlnValThrValSerSer

According to another preferred embodiment of the present invention, the variable fragment comprises the following αTT2 amino acid sequence (SEQ ID NO: 8):

GluValGlnLeuGlnAlaSerGlyGlyGly *Ser*ValGlnAlaGlyGly

SerLeuArgLeuSerCysThrAlaAlaAsnTyrAlaPheAspSerLys

ThrValGlyTrpPheArgGlnValProGlyLysGlu *Arg*GluGlyVal

Ala *GlyIleSerSerGlyGlySerThrThrAlaTyr*

*SerAspSerValLysGly*ArgTyrThrValSerLeuGluAsnAlaLys

AsnThrValTyrLeuLeuIleAspAsnLeuGlnProGluAspThrAla

IleTyrTyrCysAlaGly *ValSer*

*GlyTrpArgGlyArgGlnTrpLeuLeuLeuAla*

GluThrTyrArgPheTrpGlyGlnGlyThrGlnValThrValSerSer

In a preferred embodiment of the invention, the variable $V_{HH}$ fragment of the invention is altered in order to diminish its immunogenic properties. Such a modification can lead to an alternated immunological reaction against the $V_{HH}$ fragments of the invention when they are administered to a host either human or animal, for passive immunoprotection for example.

The invention further relates to a pharmaceutical composition comprising an immunoglobulin heavy chain variable fragment according to those which have been defined hereabove, in admixture with a physiologically acceptable vehicle.

Such pharmaceutical composition can be used for the treatment by passive immunisation, of infections or acute intoxications by toxins such as those of *Clostridium*, especially *Clostridium Botulinum* or *Clostridium Perfringens*, *Staphylococcus*, *Pseudomonas*, *Pasteurella*, *Yersinia*, *Bacillus Anthracis*, *Neisseria*, *Vibrio*, especially *Vibrio cholera*, enterotoxic *E. Coli*, *Salmonella*, *Shigella*, *Listeria* or anemonies, coral, jellyfish, spiders, beas, wasps, scorpions, snakes, including those belonging to the families of Viperidae, Crotalidae, Lapidea.

The present invention further relates to nucleotide sequences coding for a variable fragment ($V_{HH}$) of a heavy chain of an immunoglobulin devoid of light chains, obtainable by the process which has been described hereabove.

Specific nucleotide sequences are those corresponding to αTT1 and αTT2 as described in FIGS. 4A and 4B.

According to an embodiment of the invention, a preferred nucleotide sequence is the sequence contained on phasmid pHEN4-αTT2 deposited at the BCCM/LMBP collection in Belgium on Jan. 31, 1995 under no. LMBP3247.

The invention further provides means for the preparation of bivalent or even multivalent monospecific DNA constructs of variable fragments of an immunoglobulin devoid of light chains and their expression products. It thus gives access to the preparation of monovalent bispecific or multispecific variable constructs obtained from sequences encoding $V_{HH}$ fragments combined with a linker sequence. Bivalent monospecific constructs contain 2 nucleotide sequences coding for $V_{HH}$ fragments directed against the same antigen or epitope. Monovalent bispecific constructs contain on one molecule one nucleotide sequence coding for a $V_{HH}$ fragment directed against one antigen or epitope and another nucleotide sequence coding for a fragment directed against another antigen or epitope.

The corresponding expression products (protein constructs) can be obtained by genetic engenering especially by expression in host cells, like bacteria (e.g. *E. coli*) or eukaryotic cells, of the above DNA constructs.

Accordingly a variable fragment of the $V_{HH}$ type having a determined antigen specificity, can be linked to at least one further variable fragment $V_{HH}$ having a determined similar or different specificity in terms of antigen- and/or epitope specificity.

The obtained constructs (in terms of expression products) and especially the bivalent monospecific constructs advantageously offer means to improve the affinity for the antigen(s) against which they are obtained.

The linker sequence between the $V_{HH}$ fragments can be for example a sequence corresponding to the coding sequence of the hinge domain of immunoglobulin devoid of light chains (e.g. the long hinge domain) as described by (Hamers-Casterman C. et al, 1993) or a sequence derived therefrom.

As an example, in order to ligate these two variable coding sequences of $V_{HH}$ fragments to obtain monovalent bispecific construct, the sequence coding for the hinge and $CH_2$ domains, especially coding for the long hinge and $CH_2$ domains of an immunoglobulin devoid of light chains can be used. These domains have been described in WO 94/04678.

As another example, for instance for the preparation of bispecific or multispecific DNA constructs, the sequence used as linker between the $V_{HH}$ fragments is derived from the coding sequence of the hinge and is devoid of the terminal part containing nucleotides coding for the cysteine residue, or more generally devoid of the codons enabling dimerisation of the $V_{HH}$ fragment.

Preferred linkers include: the sequence starting at nucleotide 400 and ending at nucleotide 479 or between nucleotides 479 and 486 of the nucleotide sequence disclosed on FIG. 15 or the sequence starting at nucleotide 400 and ending at nucleotide 495 or between nucleotides 487 and 495 of the nucleotide sequence of FIG. 15.

The linkers can be for instance obtained by digestion of a plasmid containing the coding sequence for the $V_{HH}$, hinge and CH2 domains of an immunoglobulin devoid of light chains, with Bst EII and XmnI (or KpnI) endonucleases and further amplification of the sequence with primers annealing to each end of the hinge coding sequence as described above and illustrated in the examples.

As an example, constructs (monovalent or multivalent, monospecific or multispecific) can be obtained having a specificity with respect to two or more different toxins or generally antigens of different pathogen organisms including bacteria and viruses. . .

The invention also relates to a process for the preparation of monovalent bispecific constructs of variable fragments of a heavy chain of an immunoglobulins which comprises the following steps:

a) ligating a nucleotide sequence coding for a variable $V_{HH}$ fragment having a determined antigen- or epitop specificity to a linker nucleotide sequence to form a $V_{HH}$ linker fragment;

b) ligating the formed nucleotide sequence coding for the $V_{HH}$-linker fragment to a nucleotide sequence coding for another $V_{HH}$ fragment having a different antigen- and/or epitope-specificity, wherein the linker sequence contains the nucleotide sequence coding for part of a hinge domain wherein the codons responsible for the dimerisation of the $V_{HH}$ fragments especially by formation of a disulfide bridge between the last cysteine residues within the hinge domain are deleted.

According to a preferred embodiment, additional steps of ligation are performed with sequences coding for variable fragments ($V_{HH}$ fragments) having the same specificity or a different specificity with respect to the above fragments.

In such a case the $V_{HH}$ fragment coding sequences recovered from step b) must be digested so as to produce a nucleotide sequence having the following structure hinge linker—$V_{HH}$. In accordance $V_{HH}$—hinge linker)$_n$ coding sequences are obtained wherein n is a number higher than 2.

Preferably, the sequence encoding the hinge domain preferably the long hinge domain of the immunoglobulins devoid of light chains is the nucleotide sequence comprising or corresponding to nucleotides 400 to 479 or up to nucleotides 486 of the sequence of FIG. 15.

In a particular embodiment of the process for the preparation of bivalent or multivalent monospecific or multispecific constructs, the $V_{HH}$ fragment coding sequence linked to a nucleotide sequence encoding the hinge domain has to be amplified. Oligonucleotide primers have been defined which permit the amplification of the sequence of interest. These oligonucleotides anneal respectively with their 3' end to the beginning of the $V_{HH}$ gene or coding sequence and to the terminal part of the hinge coding sequence. Appropriate primers are for instance (SEQ ID NOS 9 & 10, respectively):

A4 (Sf I site underlined):
5'CATGCCATGACTCGCGGCCCAGCCGGCCATGGCCGA(G,T)GT(G,C)
CAGCT-3'

AM007:
5'GGCCATTTGCGGCCGCATTCCATGGGTTCAGGTTTTGG-3'

These chosen primers contain target sequences for specific endonucleases, thus allowing the cloning of the digestion products of the amplified fragments in a suitable vector.

The obtained DNA constructs are then used to transform host cells, for instance *E. coli* and the expressed proteins are then isolated and purified. The expression products of these DNA constructs are within the scope of the invention.

The heavy-chain antibodies, such as those derived from camel, and their fragments present clear advantages over other antibodies or fragments thereof derived from other animals. These are linked to the distinctive features of the heavy chain antibodies and in particular the novel fragments which can be produced by proteolytic cleavage within the hinge of these heavy-chain antibodies to generate the $V_{HH}$ and the $(V_{HH}h)2$ fragments. The $V_{HH}$ domain of a heavy chain has distinct genetic entities which confer properties of solubility not found in VH fragments derived from conventional antibodies. This property, in addition to its small size and to the fact that the amino acid sequence of the framework region is very homologous to that of human, ensures a minimum of immunogenicity. These properties would allow repetitive treatment with heavy chain $V_{HH}$ fragments for passive immunisation or antibody therapy. As mentioned above, $V_{HH}$ and the $(V_{HH}h)2$ fragments can easily be produced by proteolytic cleavage of camel immunoglobulins or via recombinant DNA technology.

The most important field of passive immunisation is intoxication due to bacterial toxins and in particular acute intoxication or intoxication due to drug resistant bacteria. Passive immunisation or treatment by antibodies is justified in those cases where vaccination is unpractical or its effects short-lived. They are particularly justified for acute intoxication which if left untreated would have lethal or cripling effects.

The following list of indications is non-exhaustive:

Tetanos due to infection by *Clostridium tetani* is an important post-trauma infection and current immunisations are not long lasting. It is also important in the veterinary field.

Botulism due to ingestion of toxins produced by *Clostridium Botulinum* and related species.

Gangrene due to infection by *Clostridium*.

Necrotic Enteritis and Enterotoxemia in humans and livestock due to *Clostridium Perfringens* ingestion.

Food poisoning due to Staphylococcal endotoxins in those cases where antibiotics are not recommended.

Pseudomonas infection refractory to. antibiotic treatment and in particular ocular infections where rapid intervention is warranted.

Diphteria toxin infection

*Pasteurella* and *Yersinia* infection causing lethal outcomes in human and livestock.

Anthrax toxin produced by *Bacillus Anthraxis* and responsible for one of the five major livestock diseases.

Infections due to other bacterial agents such as *Neisseria* or viral agents.

Furthermore, the relative resistance of the $V_{HH}$ fragment to proteolytic cleavage by digestive enzymes (e.g. pepsin, trypsin) offer the possibility of treatment against important gut pathogens, such as *Vibrio cholera* and other *vibrios*, enterotoxic *E. Coli, Salmonella* species and *Shigella* or pathogens ingested with food such as *Listeria*.

Another major target for immunotherapy is in the treatment of intoxication due to bites or contact with toxic invertebrates and vertebrates. Among the invertebrates are sea anemonies, coral and jellyfish, spiders, beas and wasps, scorpions. In the vertebrates, the venemous snakes are of particular importance and in particular those belonging to the families of Viperidae, Crotalidae and lapidea.

Passive inimunisation with partially purified immunoglobulins from immunized animals are already being used. In developiing countries, antitetanos and antidiphteria antisera are still produced on a very large scale, usually in horses. Anti-venom antibodies are produced, although on a much smaller scale, against venoms, especially snake venoms.

Another field of application is in combination with the therapeutic use of toxins in medical or surgical practice where neurotoxins such as botulinum toxin are increasingly used.

The invention also relates to the oligonucleotide primers described hereabove, either alone or in kits.

Other characteristics of the invention will appear from the figures and the examples which are described hereafter.

BRIEF DESCRIPTION OF DRAWINGS

FIG. 4A and B: Nucleotide sequence and the corresponding amino acid sequence of the two identified camel $V_{HH}$ anti tetanus toxoid clones pHEN4-αTT1 (FIG. 4A) and pHEN-αTT2 (FIG. 4B) (SEQ ID NOS 13 & 14 and 15 & 16, respectively). The framework Ser11, Phe37 and Arg or Cys 45 characteristic for the camel $V_{HH}$ heavy chain antibodies (Muyldermans et al, 1994) are underlined.

The alignment of the $V_{HH}$ amino acid sequences of camel and lama (a total of 45 sequences) was performed according to Kabat et al. The variability at each position was calculated as the number of different amino acids occuring at a given position, divided by the frequency of the most common amino acid at that position. Positions are numbered according to Kabat et al. The positions above the horizontal bar indicate the amino acids which are referrred to as (CDR1) and (CDR2) in the consensus sequence.

A variability number equal to 1 indicates a perfectly conserved amino acid at that position. The higher the variability number the more likely it will be that the amino acid at this position will deviate from the consensus sequence.

FIG. 11: Nucleic Acid Sequence of LYS2 $V_{HH}$ and translation product thereof (SEQ ID NOS 17 & 18, respectively).

FIG. 12: Nucleic acid sequence of LYS3 $V_{HH}$ and translation product thereof (SEQ ID NOS 23 & 24, respectively).

Figure 13A:
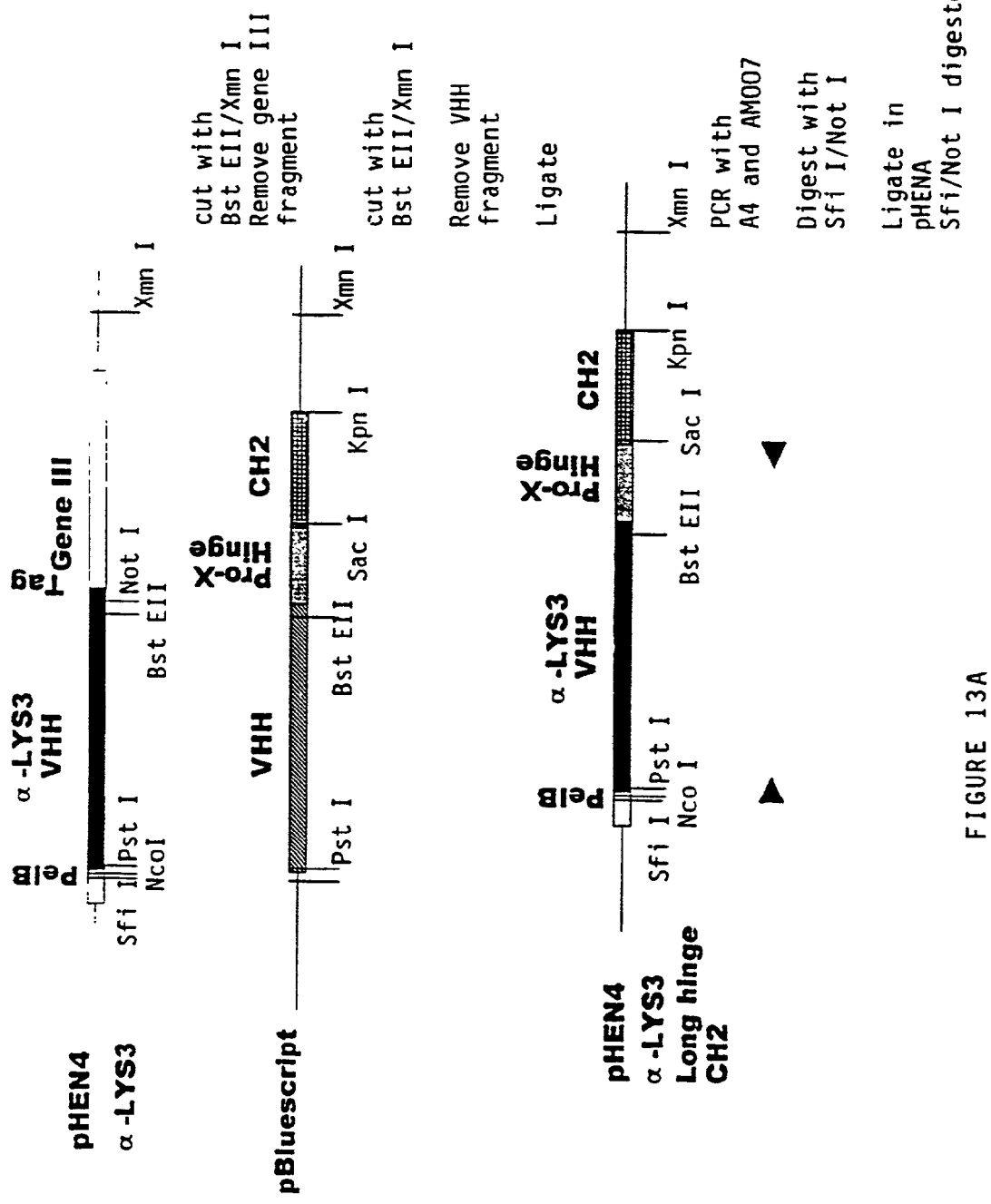

FIG. 13A: Scheme to construct the bivalent monospecific anti-LYS3 camel $V_{HH}$.

Figure 13B:
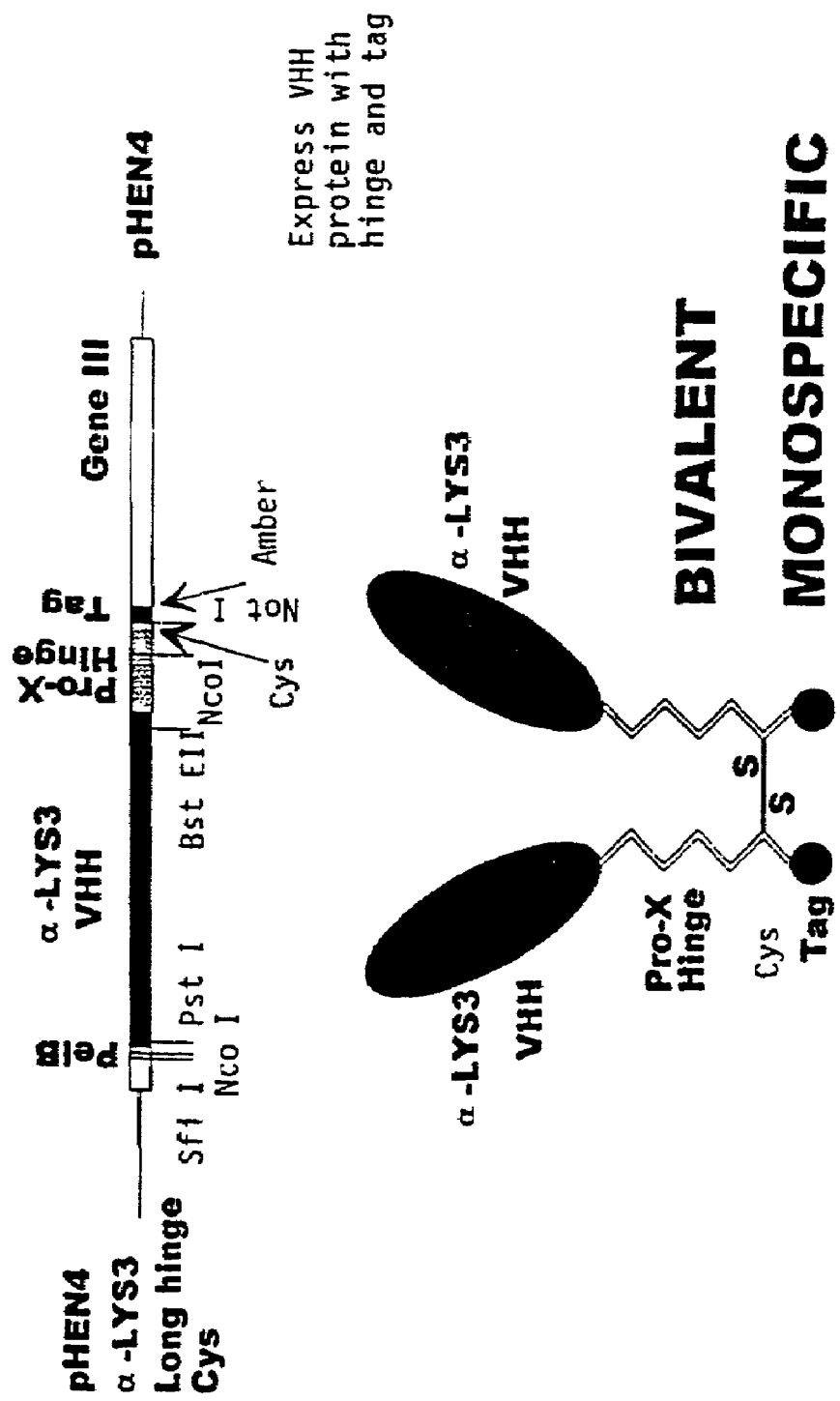

FIG. 13B: Scheme of constructed monovalent bispecific anti-LYS3-long hinge linker-anti-LYS2-Tag and schematic diagram of same.

Figure 14A:
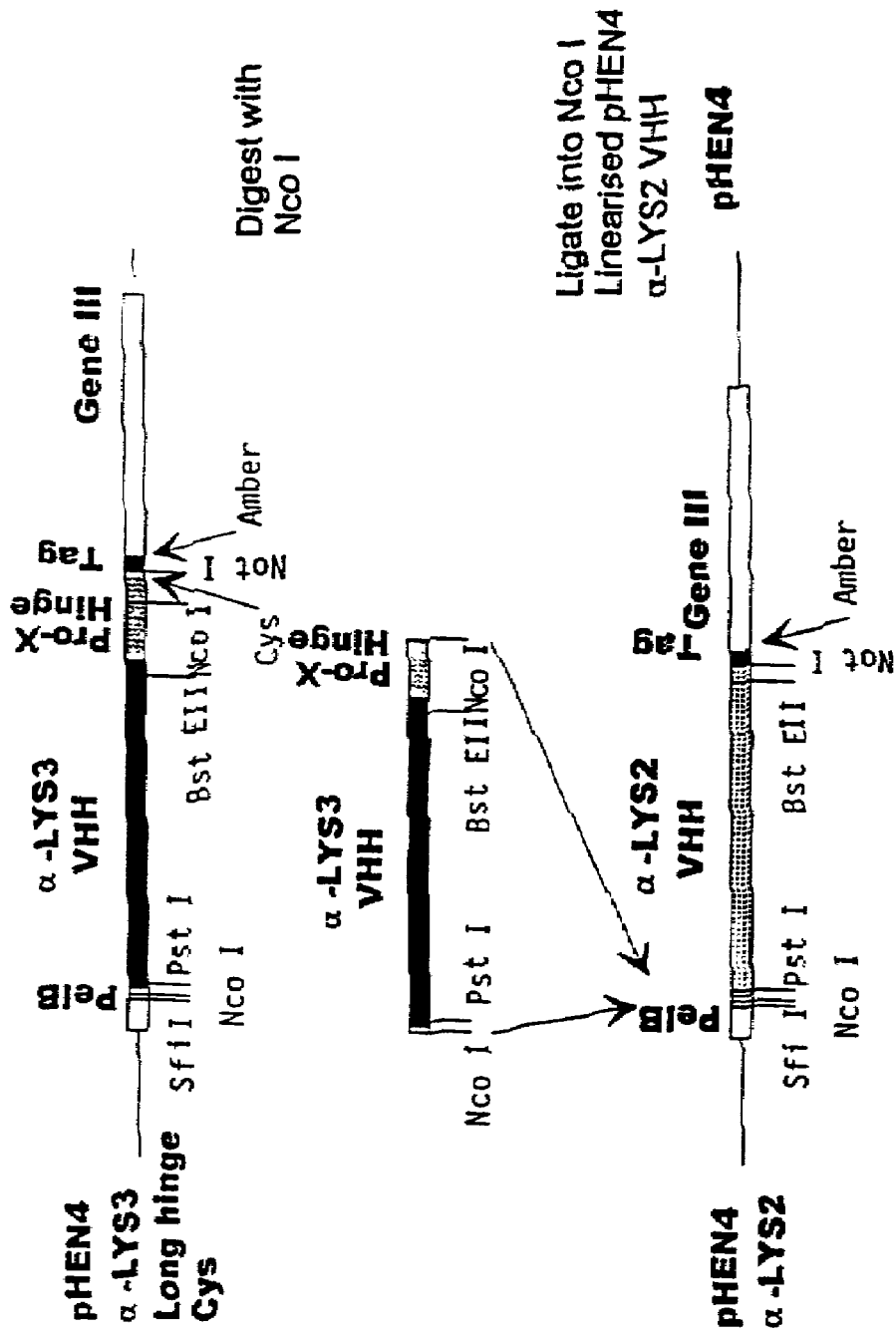

FIG. 14A: Scheme to construct the monovalent bispecific anti-LYS3-long hinge linker-anti-LYS2-Tag.

Figure 14B:
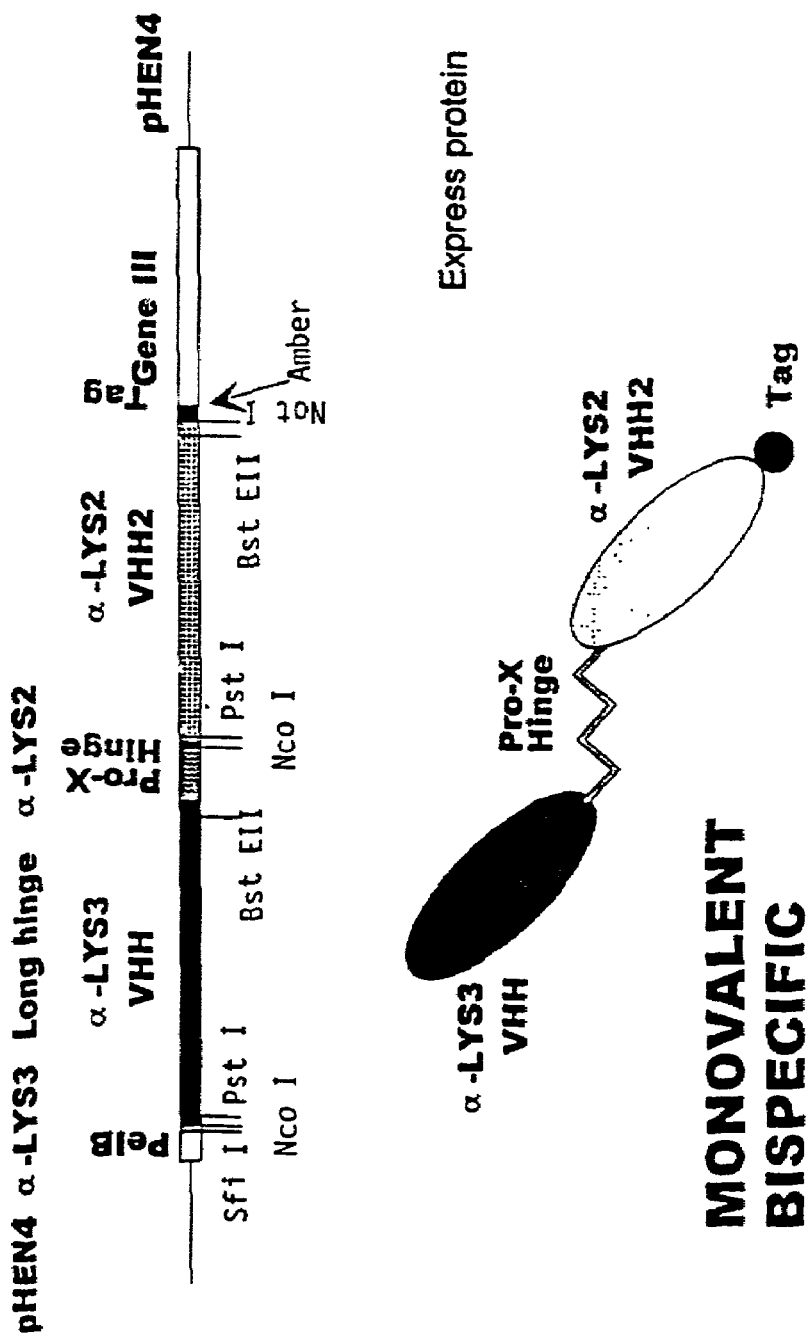

FIG. 14B: Scheme of constructed monovalent bispecific anti-LYS3-long hinge linker-anti-LYS2-Tag and schematic diagram of same.

Figure 15B:

FIG. 15: Nucleotide and amino acide sequence (SEQ ID NOS 21 & 22, respectively) of the anti-LYS3-long hinge/Cys-Tag. This protein will spontaneously dimerise.
double underlined: amino acids specific for camellid $V_{HH}$
Boxed: CDR's
underlined with dashes: long hinge linker
underlined: Tag
Boxed S: Cysteine which is involved in the interdomain disulfide bond.

FIG. 16: Nucleotide and amino acid sequence (SEQ ID NOS 23 & 24, respectively) of the anti-LYS3-long hinge linker-anti-LYS2-Tag polypeptide.
For underlining and boxes see legend FIG. 15.

DETAILED DESCRIPTION OF THE INVENTION

EXAMPLE I

Generation of Specific Camel $V_{HH}$ Fragments Against Tetanus Toxoid

In this application, results are presented, which prove the feasibility of generating specific camel $V_{HH}$ fragments with demonstrated folding and good binding affinity. This was done by generating a library of camel fragments derived from the dromedary IgG2 and IgG3 isotype, display of the $V_{HH}$ library on phage as fusion proteins with the gene III protein of bacteriophage M13 to allow selection of the antigen binders, and finally of expressing and extracting the soluble and functional $V_{HH}$ fragments from E.coli. As antigen, we choose the tetanus toxoid was chosen because comparisons are possible with published data. In addition, the tetanus toxoid is a highly immunogenic protein that is routinely used as a vaccine in humans to elicit neutralizing antibodies. The two camel $V_{HH}$ fragments that were identified were specific and of high affinity. The affinities of the two camel $V_{HH}$ fragments appear to be comparable with those from the human anti-tetanus toxoid $F_{AB}$'s recently obtained by Mullinas et al. (1990) and by Persson et al. (1991).

Camel Immunization

The serum of a camel (Camelus dromedarius) was shown to be non-reacting with tetanus toxoid (RIT, Smith Kline Beecham, Rixensart, Belgium). This camel was injected with 100 μg tetanus toxid at days 9, 30, 52, 90 and with 50 μg at days 220, 293 and 449. The blood was collected 3 days after each injection.

mRNA Purification of Camel Blood Lymphocytes

Peripheral blood lymphocytes were purified with LYMPHOPREP (Nycomed, Pharma) from the bleeding at day 452. Aliquots of $1.10^6$-$5.10^6$ cells were pelleted and frozen at $-85°$ C. and subsequently used as an enriched source of B-cell mRNA for anti-tetanus toxoid.

The mRNA was prepared from a total of $10^6$ peripheral blood lymphocytes either by the "Micro FastTrack" mRNA isolation kit (Invitrogen) or the "QuickPrep Micro mRNA Purification" kit of Pharmacia, following the recommendations of the manufacturer. With both protocols, up to a few μgr of mRNA was obtained which was used in the subsequent cDNA synthesis step.

cDNA Synthesis and PCR Amplification of Camel $V_{HH}$ Gene

The first-strand cDNA was synthesized with the Invitrogen "cDNA-cycle" or the Pharmacia "Ready-To-Go" kit. The first-strand cDNA was used immediately afterwards for the specific amplification of the camel $V_{HH}$ region by PCR. The primers used have following sequences: the BACK primer (SEQ ID NO: 1) (5'-GA TGTGCAG CTGCAGGCGTCTGG(A/G)GGAGG-3'), the internal PstI site is underlined) is designed to hybridize to the framework 1 region (codons 1 to 10) of the camel $V_{HH}$' while the FOR primer (SEQ ID NO: 11) (5'-CGCCATCAAGGTACCAGT-TGA-3') hybridizes in the CH2 region. The PCR was carried out with the Taq polymerase from Boehringer Mannheim.

Figure 1:
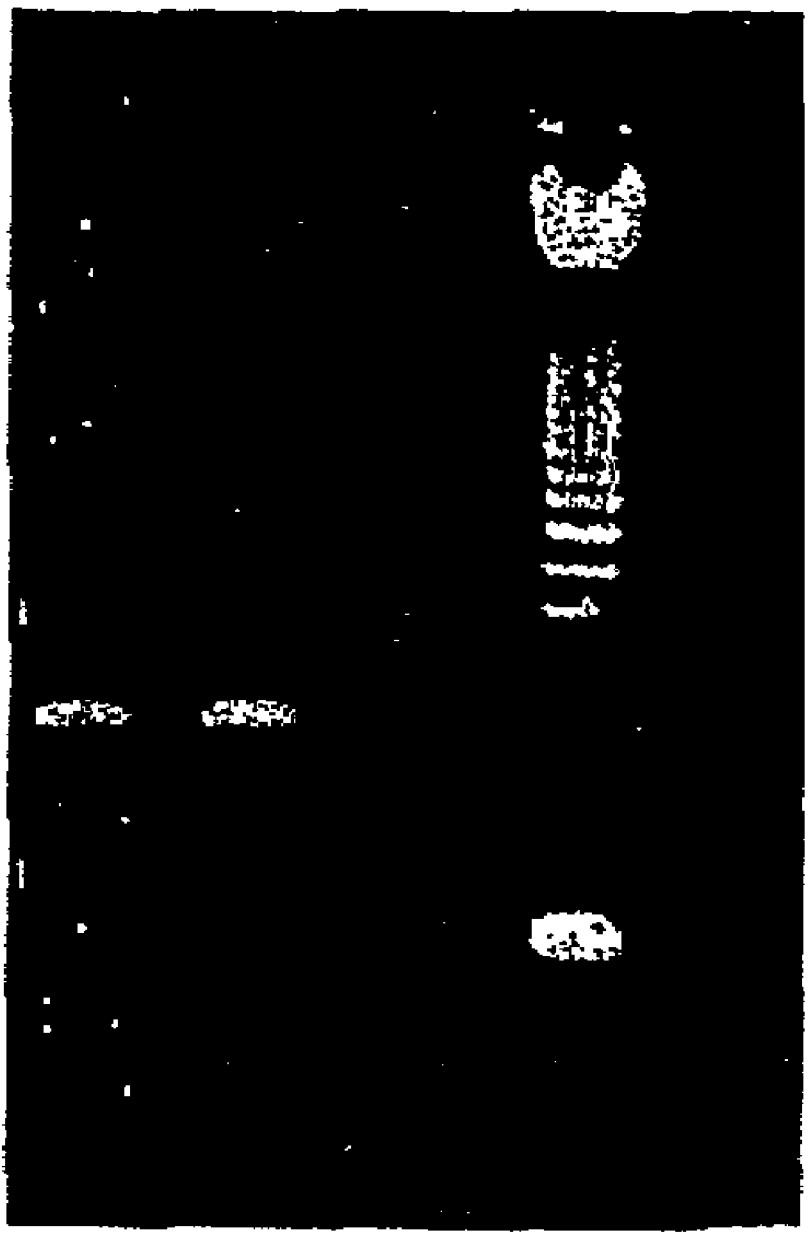
FIG. 1: 1% agarose gel electrophoresis of the PstI/BstEII digested PCR amplification product of the camel $V_{HH}$ gene (lanes 1 and 2) next to the 123 bp ladder of BRL used as a size marker (lane 4). The PCR product comigrates with the $3^{rd}$ band of the marker, 369 bp in length.
Figure 2:
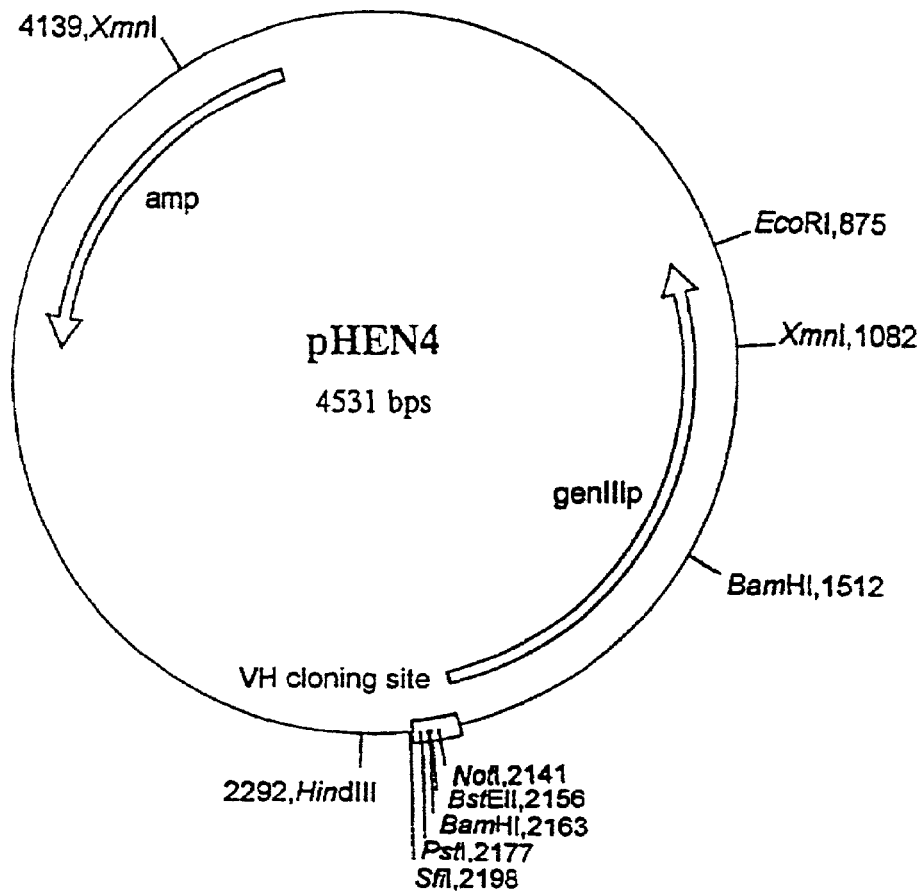
FIG. 2: Map of the pHEN4 with the nucleotide sequence of the $V_{HH}$ cloning site shown in the lower part of the figure (SEQ ID NOS 27-29, respectively). The PstI and BstEII sites can be used to clone the camel $V_{HH}$ PCR product shown in FIG. 1.

The PCR product was purified according to standard protocols (Sambrook et al., 1989) and digested with the PstI restriction enzyme of which the target site occuffed in the BACK primer, and with BstEII which has a naturally occurring site in the framework 4 of the camel $V_{HH}$ regions. The resulting fragments of approximately 360 bp (FIG. 1) were ligated into the pHEN4 vector cut with the same restriction enzymes. The pHEN4 vector (FIG. 2) is the pHEN1 plasmid (Hoogenboom et al., 1991)—a pUC119 based vector—where the myc-tag was replaced by the decapeptide tag present in the IMMUNOZAP H vector (Stratacyte). Also the polylinker was modified to allow the cloning of the camel $V_{HH}$ gene between a PstI and a BstEII site located after the PelB leader signal and in front of the decapeptide tag and gene III of bacteriophage M13.

Construction of a Camel $V_{HH}$ Library

The ligated DNA material was precipitated with 10 volumes and resuspended in 10 μl water and electrotransformed in E.coli XL1 Blue MRF' cells (Stratagene). After electroporation according to the recommended protocol (Stratagene) we kept the cells for 1 hour at 37° C. in 1 ml SOC medium before plating on LB plates containing 100 μg ampicilline/ml. After an over night incubation at 37° C. the transformed cells were grown out into colonies and some 500,000 recombinant clones were obtained. About 20 colonies, randomly selected, were toothpicked and grown in selective medium (LB/Ampicilline) to prepare plasmid DNA and to check their insert by sequencing. For each clone tested, we found a different $V_{HH}$ region with the aminoacid sequence and contents characteristic for a $V_{HH}$ originating from a camel heavy chain immunoglobulin (Muyldermans et al., 1994). This indicates that a vast camel $V_{HH}$ library was generated.

The remaining 500,000 clones were scraped from the plates with a minimal amount of LB containing 50% glycerol and stored at $-85°$ C. until further use.

Panning with Tetanus Toxoid

Figure 3:
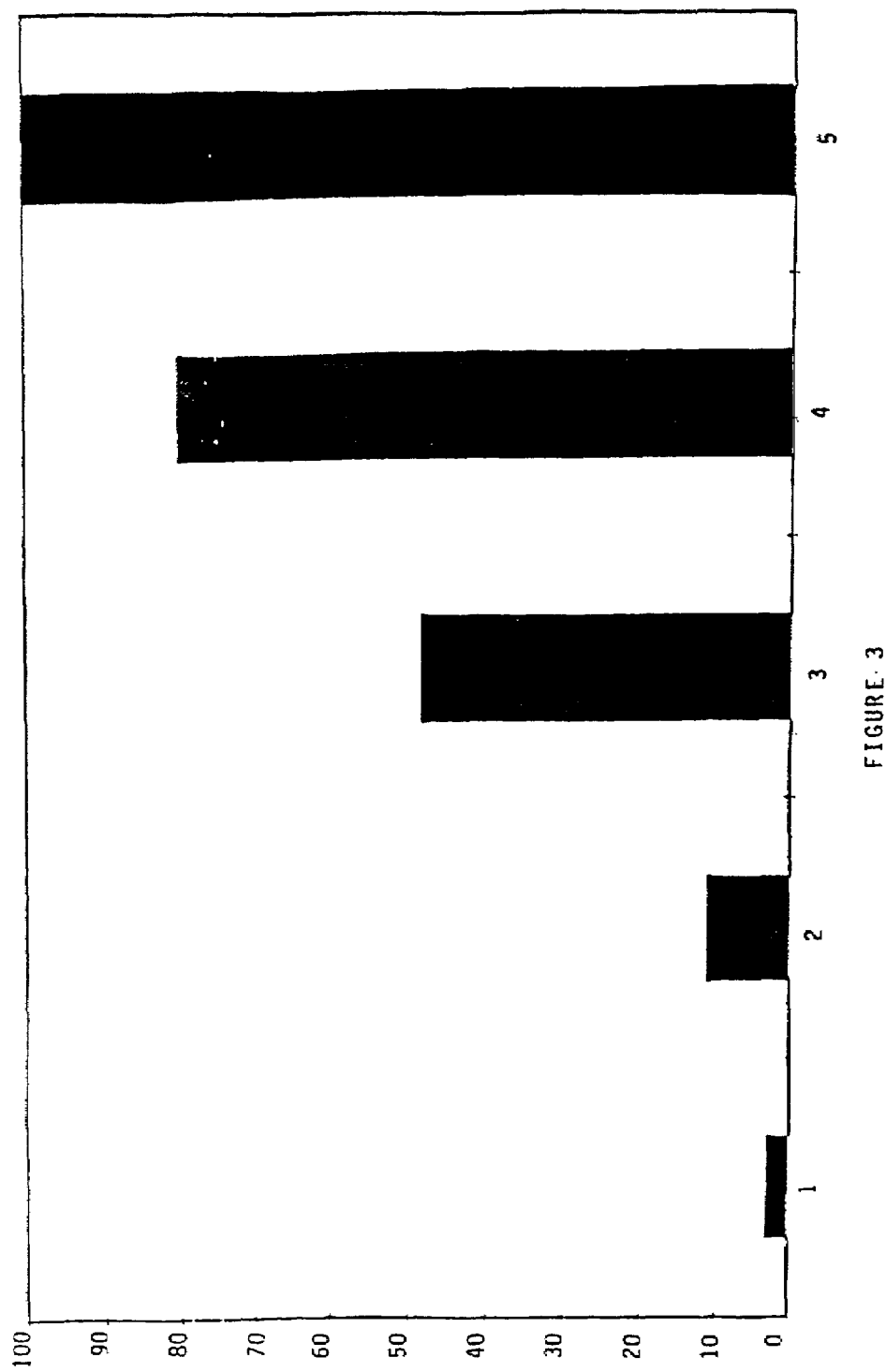
FIG. 3: 100 individual clones were randomly selected from the original camel $V_{HH}$ library (0), or after the first (1), second (2), third (3) or fourth (4) round of panning. After M13 infection the virions were tested for binding activity against immobilized tetanus toxoid. The number of positive clones are shown as a function of number of pannings.

The library was screened for the presence of anti-tetanus toxoid camel $V_{HH}$'s by panning. To this end, approximately $10^9$ cells (=5 ml suspension of the frozen recombinant clones) were grown to midlogarithmic phase in 200 ml of LB medium supplemented with 1% glucose and 100 μg ampicillin/ml before infection with M13K07 bacteriophages. After adsorption of the bacteriophages on the E.coli cells for 30 min at room temperature, the cells were harvested by centrifugation and washed in LB medium supplemented with ampicilline and kanamycin (25μg/ml). The cells were incubated overnight at 37° C. to secrete the recombinant pHEN phasmid, packaged within the M13 virion containing a camel $V_{HH}$ fused to some of its M13 gene III proteins (Hoogenboom et al., 1991). The phagemid virions were prepared according to the protocol described by Barbas et al. (1991). The phage pellets were resuspended in blocking solution (1% casein in phosphate buffered saline, PBS), filtered through a 0.2 μm filter into a sterile tube and used for panning. For the panning the Falcon 3046' plates were coated overnight with 0.25 mg/ml or 2 mg/ml tetanus toxoid dissolved in PBS or hydrogencarbonate pH 9.6. The wells were subsequently washed and residual protein binding sites were blocked with blocking solution at room temperature for 2 hours. The adsorption of the phagemid virions on the immobilized antigen and the washing and elution conditions were according to Marks et al (1991) or were taken from the protocol described by the <<Recombinant Phage Antibody System>> of Pharmacia 4 consecutive rounds of panning were performed. After the fourth round of panning the eluted phagemid virions were added to exponentially growing TG1 cells (Hoogenboom et al. 1991) and plated on ampicillin containing LB plates. After overnight growth several colonies were grown individually in LB medium to midlogarithmic growing phase, and infected with M13K07 helper phage. The virions were prepared and tested for their binding activity against tetanus toxoid immobilised on microtiter plates. The presence of the virion binding to the immobilized antigen was revealed by ELISA using a Horse RadishPeroxidase/anti-M13 conjugate (Pharmacia). The percentage of binders was increasing after each round of panning. In the original library we found 3 clones out of 96 which showed binding with the immobilizes tetanus toxoid. This number was increased to 11, 48 and 80 after the first, second and third round of panning. All of the individual clones which were tested after the fourth round of panning were capable of recognizing the antigen, as measured by ELISA (FIG. 3). Ten positive clones were grown and tested by PCR to check the presence of an insert with the proper size of the $V_{HH}$ gene, and their DNA was finally sequenced. The sequencing data revealed that two different clones were present among this set of 10 clones. The phasniid DNA of these clones was named pHEN4-αTT1 and pHEN4-αTT2, (The pHEN4-αTT2 phasmid DNA was deposited at the "BelgianCoordinated Collections of Microorganisms" BCCM/LMBP on Jan. 31, 1995 under accession number LMBP3247), and it was shown that these two different clones contained a cDNA coding for a camel $V_{HH}$ (FIG. 4). Comparison of the amino acids in these clones with the camel $V_{HH}$ clones analysed before (Muyldermans et al., 1994) clearly indicated that the anti-tetanus camel $V_{HH}$ originated from a heavy chain inimunoglobulin lack the CH1 domain and light chains. Especially the identity of the key residues at position 11 (Ser), 37 (Phe) and 45 (Arg or Cys) and 47 (Leu or Gly) proved this statement (Muyldermans et al., 1994).

Production of Soluble Camel $V_{HH}$ with Anti-Tetanus Toxoid Activity

Figure 5:
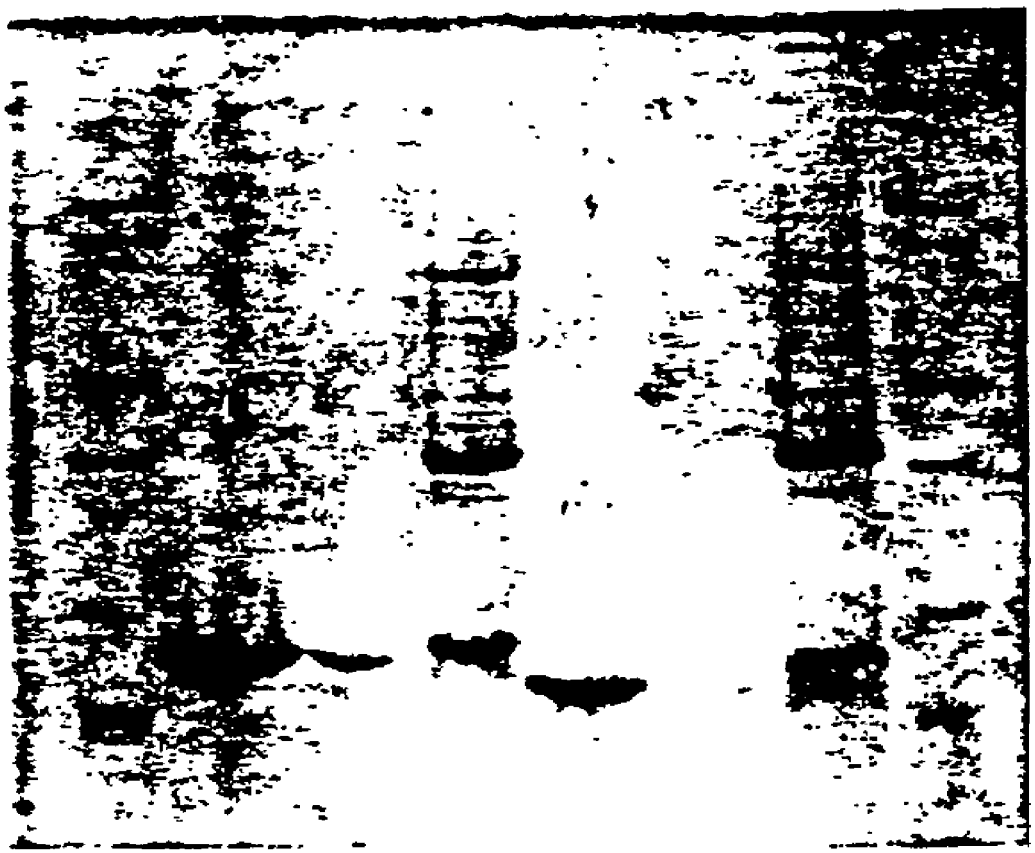
FIG. 5: SDS-polyacrylamide gel electrophoresis of the proteins extracted from the periplasm of WK6 cultures induced with IPTG. Lane 1 & 8, protein size marker (Pharmacia) MW are (from top of to bottom) 94,000; 67,000; 43,000; 30,000; 20,100 and 14,400 D. Lanes 2 and 7 Expressed periplasmic proteins extracted from WK6 cells containing pHEN4-αTT2' and pHENA-αTT1' cloning vector. Lane 3 & 4, Purified $V_{HH}$ domain of pHEN4-αTT2 at 10 and 1 microgram. Lanes 5 & 6, Purified $V_{HH}$ domain of pHEN4-αTT1 at 10 and 1 migrogram. The position of the expressed soluble camel VH protein is indicated with an arrow. It is clearly absent in the second lane.

The phasmid DNA of the two clones which scored positive in the tetanus toxoid ELISA were transformed into WK6 cells. These cells are unable to suppress the stopcodon present in the vector between the decapeptide tag and the gene III protein. The WK6 *E.coli* cells harboring the pHEN4-αTT1 or pHEN4-αTT2 phasmid were grown at 37° C. in 1 liter of TB medium with 100 mgr ampicillin/ml and 0.1% glucose. When the cells reached an $OD_{550}$ of 1.0 we harvested the cells by centrifugation at 5000 rpm, 10 minutes. The cell pellet was washed once in TB medium with ampicillin, but omitting the glucose. The cells were finally resuspended in 1 liter of TB medium with ampicillin (100 μg/ml). We induced the expression of the camel $V_{HH}$ domain by the addition of 1 mM IPTG and further growth of the cells at 28° C. for 16 hours. The expressed proteins were extracted from the periplasmic space following the protocol described by Skerra and Plucthun (1988). We pelleted the *E.coli* cells by centrifugation at 4000 g for 10 min (4° C.). The cells were resuspended in 10 ml TES buffer (0.2 M Tris-HCl pH 8.0, 0.5 mMEDTA, 0.5 M sucrose). The suspension was kept on ice for 2 hours. The periplasmic proteins were removed by osmotic shock by addition of 20 ml TES diluted ¼ with water. The suspension was kept on ice for 1 hour and subsequently centrifuged at 12,000 g for 30 minutes at 4° C. The supernatant contained the expressed camel $V_{HH}$ domain. The extract corresponding to 400 μl cell culture' was applied under reducing conditions on a SDS/polyacrylamide protein gel. The extracted proteins were visualized in the SDS/polyacrylamide gels by Coomassie blue staining (FIG. 5). A protein band with an apparent molecular weight of 16,000 D was clearly present in the *E.coli* cultures containing the recombinant clones and induced with IPTG. Alternatively, the presence of the camel $V_{HH}$ proteins in the extract was revealed with IPTG. Alternatively, the presence of the camel $V_{HH}$ proteins in the extract was revealed by Western blot using a specific rabbit anti-camel $V_{HH}$ or rabbit anti-dromedary IgG serum or the anti-tag antibody.

We estimate from the band intensity observed in the Coomassie stained gel that more than 10 mg of the camel $V_{HH}$ protein (non-purified) can be extracted from the periplasm of 1 liter induced *E.coli* cells.

Figure 6:
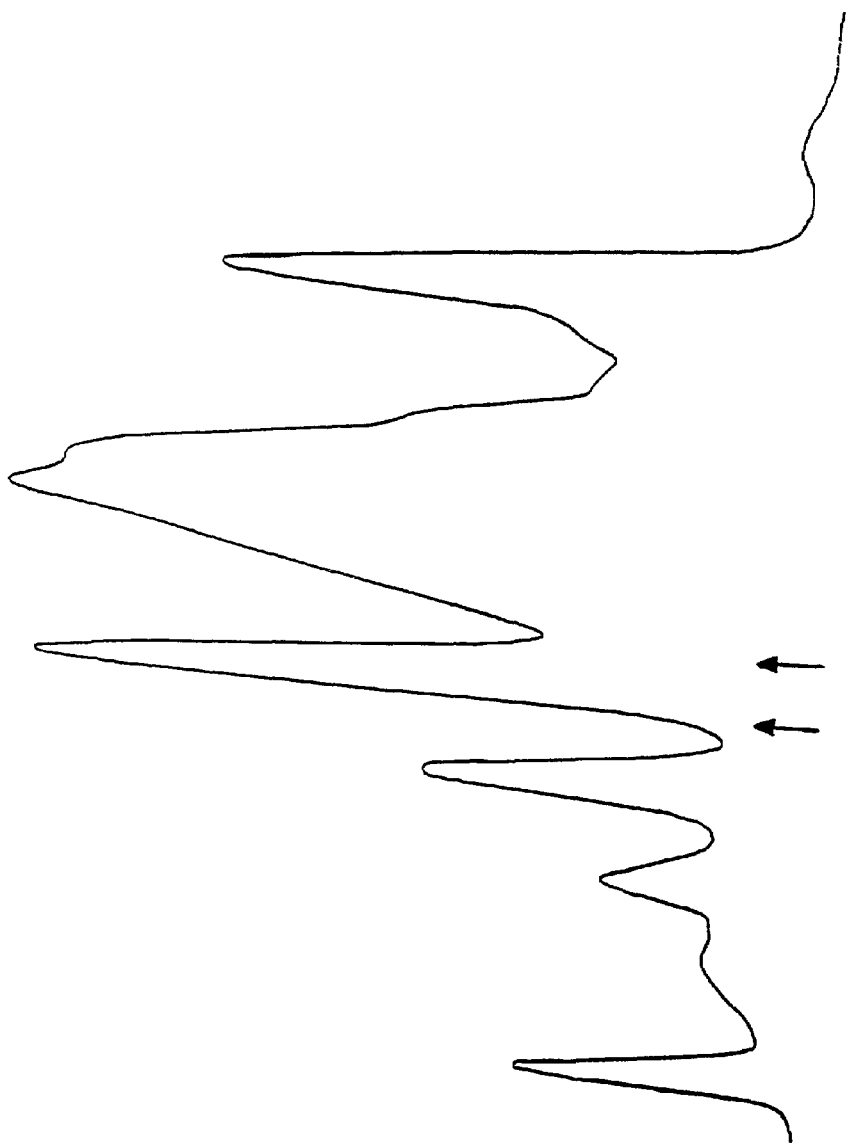
FIG. 6: The total periplasmic extract of 1 liter of culture of WK6 cells carrying the pHEN4-αTT2 was concentrated to 5 ml and fractionated by gel filtration on SUPERDEX 75 (Pharmacia) using 150 mM NaCL, 10 mM sodium phosphate pH7.2 as eluent. The pure $V_{HH}$ is eluted at the fractions between the arrows.

For the purification of the anti-tetanus toxoid camel $V_{HH}$ we concentrated the periplasmic extract 10 times by ultrafiltration (Milipore membrane with a cut off of 5000 Da). After filtration the concentrated extract from the pHEN4-αTT2 was separated according its molecular weight by gel filtration on SUPERDEX-75 (Pharmacia) (FIG. 6) equilibrated with PBS (10 mM phosphate buffer pH7.2, 150 mM NaCl). The peak containing the anti-tetanus toxoid activity eluted at the expected molecular weight of 16,000 Da indicating that the protein behaved as a monomer and doesn't dimerize in solution. The fractions containing the pure $V_{HH}$ (as determined by SDS-PAGE) were pooled and the concentration was measured spectrophotometrically using a calculated $E_{280}$ (0.1%) of 1.2 and 2.3 respectively for the αTT1 and αTT2. From the UV absorption at 280 nm of the pooled fraction we could calculate a yield of 6 mgr of purified protein per liter of bacterial culture. The purified protein could be further concentrated by ultrafiltration to 6 mgr/ml in PBS or water without any sign of aggregation, as seen on the UV spectrum.

Concerning the expression yield in *E.coli* it should be realized that at this stage we didn't try to optimize the expression or the protein extraction conditions. However, as the yield of the purified αTT2 camel $V_{HH}$ reached 6 mgr per liter of bacterial culture, and as we obtained the soluble protein at a concentration of 6 mgr/ml, it is clear that the expression is comparable or better than other scFv's or $F_{AB}$'s expressed in *E.coli*. Furthermore, the solubility of the camel $V_{HH}$ αTT2 is certainly better than that obtained for the mouse VH fragments. The yield and solubility is certainly in the range needed for most applications.

Figure 7:
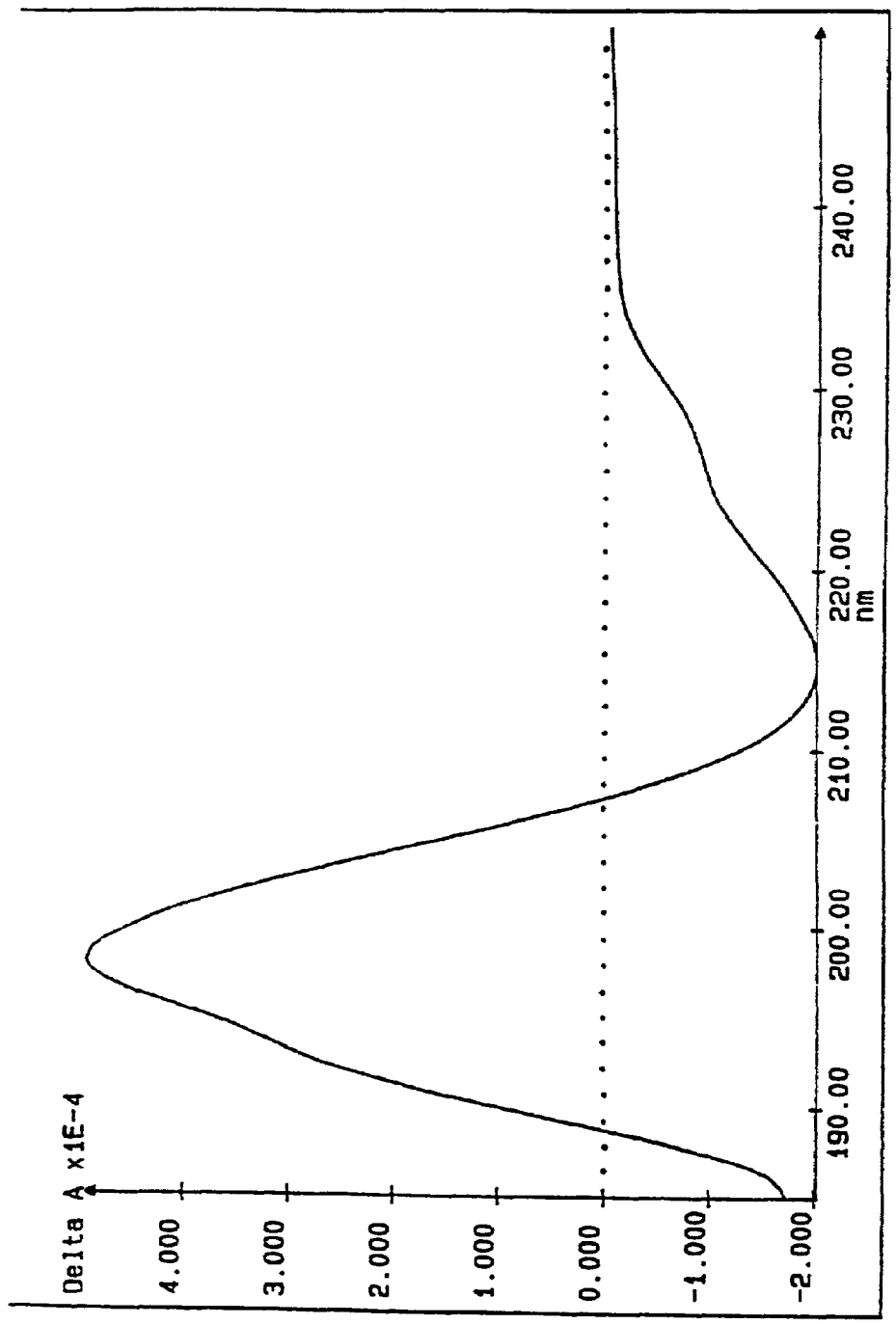
FIG. 7: CD (Circular dichroism) spectrum (Absorbance versus wavelength in nm) of the purified $V_{HH}$ domain αTT2 at $3.9 \times 10^{-6}$ Min water measured in a cuvette with a pathlength of 0.2 cm. The negative band near 217 and 180 nm and the positive band around 195 nm are characteristic for β structures (Johnson, 1990).

To prove the proper folding of the purified protein, the αTT2 was brought at a concentration of $3.9 \times 10^{-6}$ M and used it for CD measurement (FIG. 7). The CD spectrum is characteristic for a polypeptide with a β-pleated sheet folding as expected for a well structurated immunoglobulin fold (Johnson, 1990).

The Camel Anti-Tetanus Toxoid $V_{HH}$ Affinity Measurements

The binding of the camel $V_{HH}$ antibody to the tetanus toxoid immobilised on the microtiter plates was revealed by the successive incubation with firstly, the rabbit anti-camel $V_{HH}$ or rabbit anti-dromedary IgG and secondly a goat anti-rabbit/alkaline phosphatase conjugated antibodies (Sigma). The apparent affinity of the camel $V_{HH}$ proteins against tetanus toxoid was estimated by inhibition ELISA exactly as described by Persson et al. (1991) for the human anti-tetanus toxoid FAB fragments they produced in *E.coli*

Figure 8:
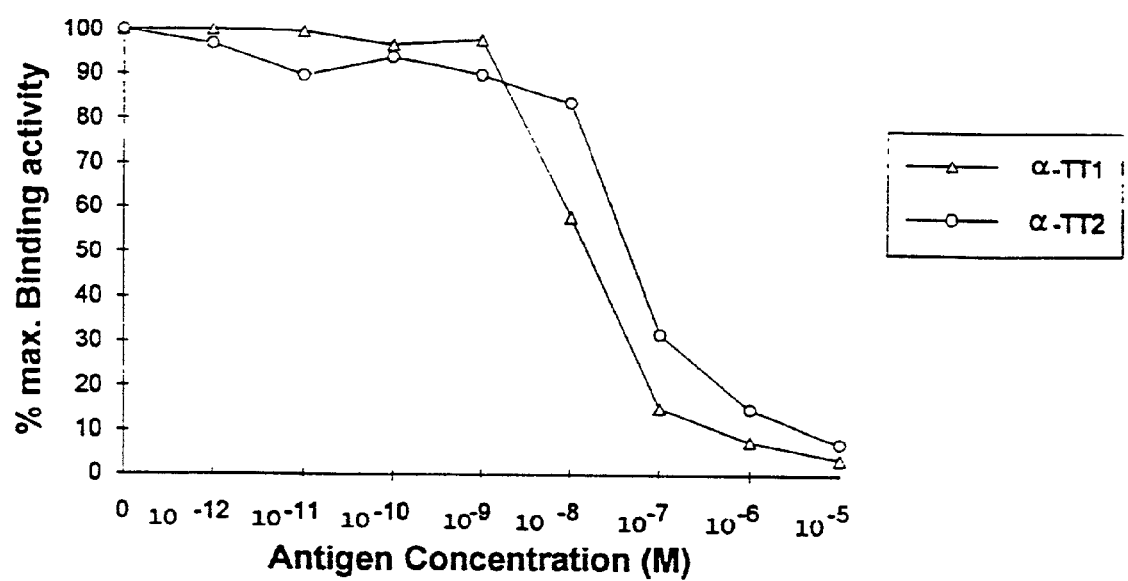
FIG. 8: Specificity of antigen binding shown by competitive ELISA. The experiments were carried out in triplicate with the bacterial periplasmic extracts of pHEN4-αTT1 and pHEN4-αTT2.

The specificity of the soluble camel $V_{HH}$ for the tetanus toxoid was suggested from the ELISA experiments in which we competed the binding with free antigen was competed. An apparent inhibition constant of around $10^{-7}$, $10^{-8}$ M was observed for both $V_{HH}$ fragments (FIG. 8). This compares favorably with the inhibition constants for the human anti-tetanus toxoid $F_{AB}$ fragments cloned by Persson et al. (1991) which were in the range of $10^{-7}$ to $10^{-9}$ M.

The measurement of the affinity constant by ELISA is however, more reliable if determined according to the procedure of Friguet et al. (1987). With this protocol we found an affinity constant of $6.10^7 M^{-1}$ and $2.10^7 M^{-1}$ for the αTT1 and αTT2 respectively. These affinities are consistent with a specific $V_{HH}$-antigen interaction (the polyspecific antibodies generally bind their antigen with affinities of $10^6 M^{-1}$ or less (Casali et al. 1989)).

Epitope Recognition of αTT1 and αTT2.

Tetanus toxin consists of three domains. The C fragment binds to the neuronal cells, it is said to be the neurospecific binding domain. The B domain appears to be involved in the neuronal penetration of the A domain or L chain (Montecucco & Schiavo, 1993). The L chain is responsible for the intracellular activity.

The C fragment is the most immunogenic part of the tetanus neurotoxin, and a recombinant C fragment is commercially available (Boehringer and Callbiochem). We showed by ELISA that the αTT1 bacterial extract binds equally well both to the complete tetanus toxoid and to the recombinant C fragment. Therefore the epitope of this camel $V_{HH}$ is present on the C fragment. By contrast, the αTT2 extract binds to the complete tetanus toxoid, but not to the C fragment. Therefore the αTT2 recognizes an epitope located on the A or B domain.

The in vivo Neutralization of Tetanus Toxin Toxicity.

Figure 9:
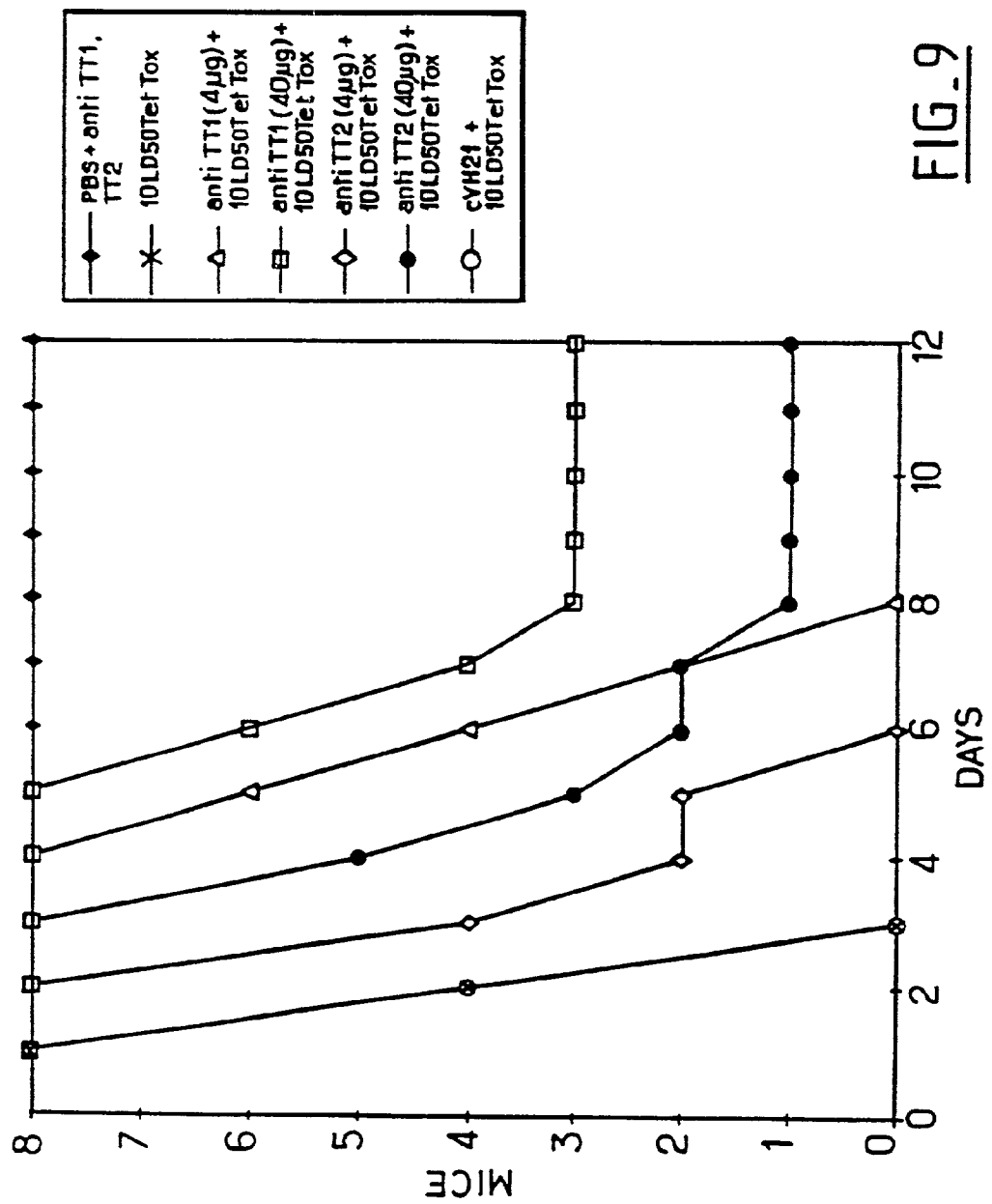
FIG. 9: Number of mice surviving after I.P injection of 100 ngr tetanus toxin (10× LD50) or co-injection of tetanus toxin with the purified $V_{HH}$ αTT1, αTT2 or the non-specific cVH21 (Muyldermans et al., 1994) at 4 or 40 microgram.
Figure 10:
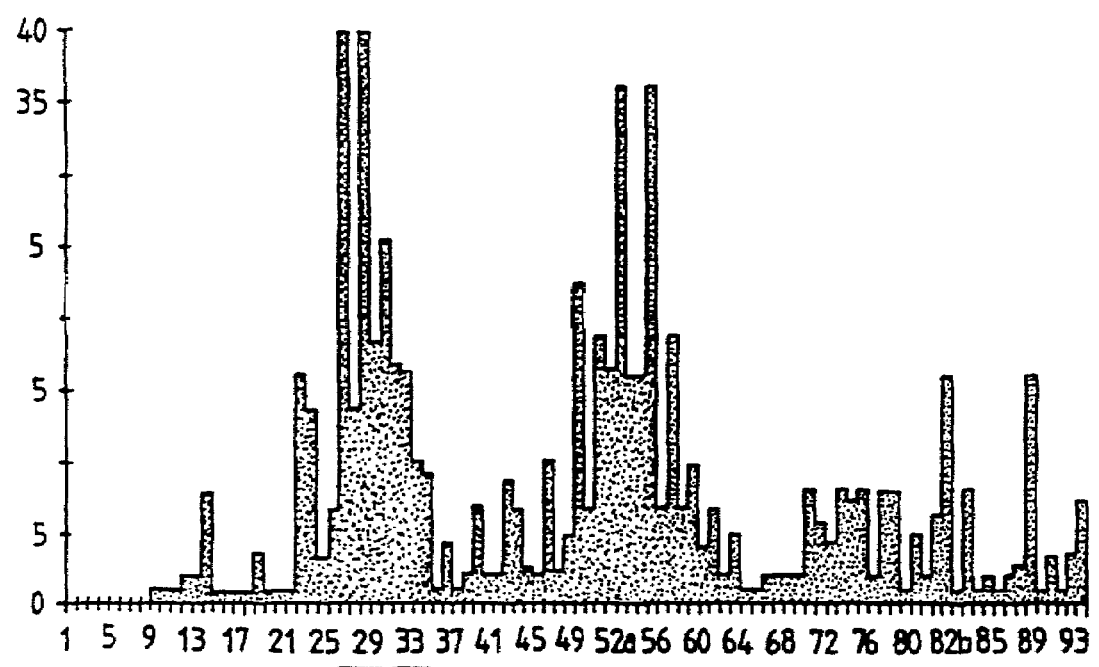
FIG. 10: Variability plot of the camelid $V_{HH}$ sequence (CDR3 and framework 4 regions are not included).

The neutralizing activity of the purified camel αTT1 or αTT2 $V_{HH}$ domains against tetanus toxin was tested. As a control, eight NMRI mice of 8 to 12 weeks (80 to 100 g) were injected I.P. with 400 ng tetanus toxin (SmithKline Beecham Biologicals) (=10 times the LD50) in 0.1 ml PBS. To test the neutralizing activity of the camel $V_{HH}$ αTT1 or αTT2 we preincubated 4 or 40 mg of this purified recombinant protein with 400 ng of the tetanus toxin in 0.1 ml of PBS for 30 minutes before I.P. injection into the mice. The survival of the mice was followed over a period of 2 weeks (FIG. 9). It is clear that all mice injected with the tetanus toxin alone or in the presence of a non-specific purified camel $V_{HH}$ (cVH21 of Muyldermans et al., 1994) were killed within 3 days. The survival of the mice injected with the tetanus toxin was increased significantly by the co-injection of only 4 mg of the purified camel αTT1 or αTT2. The survival was even more pronounced for the co-injection of tetanus toxin with 40 mg of camel $V_{HH}$. It appears that the αTT1 had a slightly higher neutralizing activity than the αTT2. This could originate from its intrinsic higher affinity for binding the tetanus toxin (Simpson et al., 1990). Alternatively it might result from the binding of the αTT1 $V_{HH}$ to the fragment C of the tetanus toxin which inhibits more the toxic effect than the binding of the αTT2 to its epitope outside the C fragment.

EXAMPLE II

Generation of Specific Camel $V_{HH}$ Fragments Against Lysozyme

Using the same protocol as the one described in Example I (specific steps or conditions modifying those of example I are indicated hereafter) for the generation of specific camel $V_{HH}$ fragments having a specificity and an affinity for tetanus toxoid, $V_{HH}$ fragments have been obtained against lysozyme.

We choosed the Hen Egg Lysozyme (HEL) as an antigen to immunize a camel (*Camelus dromedarius*). This protein was selected for the reason that comparisons can be made with several other mouse monoclonal antibody fragments recognizing the same antigen and of which the structure even in complex with its antigen are known.

Camel Immunization

The serum of a camel was shown to be non-reacting with lysosyme. We injected this camel with 100 µg lysozyme (Boehringer) at days 9, 30, 52, 90 and with 50 µg at days 220, 293 and 449. The blood was collected on average 3 days after each injection.

The following steps were then performed as in Example 1.
mRNA purification of camel blood lymphocytes.
cDNA synthesis and PCR amplification of camel $V_{HH}$ gene.
Construction of Camel $V_{HH}$ library.
Panning with lysozyme (the Falcon 3046' plates were coated with 1 mg/ml lysozyme).
96 colonies were randomly chosen and grown individually in LB medium.
The virions were prepared and tested for their binding activity against lysozyme immobilised on microtiter plates.

The percentage of binders was increased after each round of panning. Twenty positive clones were grown and tested by PCR to check the presence of an insert with the proper size of the $V_{HH}$ gene, and their DNA was finally sequenced. The sequencing data revealed that two different clones were present among this set of 10 clones. The phasmid DNA of these clones was named pHEN4-☐LYS2 and pHEN4-☐LYS3, and it was shown that these two different clones contained a cDNA coding for a camel $V_{HH}$ (FIGS. 11, 12). Comparison of the amino acids in these clones with the camel $V_{HH}$ clones we analysed before (Muyldermans et al., 1994) clearly indicated that the anti-lysozyme camel $V_{HH}$ originated from a heavy chain immunoglobulin lacking the CH1domain and light chains. Especially the identity of the key residues at position 11 (Ser), 37 (Phe), 44 (Glu), 45 (Arg) and 47 (Gly) proved this statement (Muyldermans et al., 1994).

Production of soluble camel $V_{HH}$ with anti-lysozyme activity.

For the purification of the anti-lysozyme camel $V_{HH}$ we concentrated the periplasmic extract 10 times by ultrafiltration (Milipore membrane with a cut off of 5000 Da). After filtration the concentrated extract from the pHEN4-αLYS2 can be purified by Protein A-SEPHAROSE chromatography. Elution of the αLYS2 $V_{HH}$ is done with 100 mM Tri-ethanol amine. The pH of eluate is immediately neutralized with 1 M Tris-HCl (pH 7.4). Unfortunately the expressed α-LYS3 $V_{HH}$ does not bind to Protein A. Therefore the purification has to be performed by affinity chromatography. The concentrated extract is applied on a column of lysozyme immobilized on CNBr-SEPHAROSE (Pharmacia). Elution of the anti-lysozyme $V_{HH}$ is obtained with 100 mM Tri-ethanolamine. The eluate has to be neutralized as described above. Further purification of both anti-lysozyme $V_{HH}$'s can obtained by gel filtration on SUPERDEX-75 (Pharmacia) equilibrated with PBS (10 mM phosphate buffer pH7.2, 150 mM NaCl). The peak containing the anti-lysozyme activity eluted at the expected molecular weight of 16,000 Da indicating that the protein behaved as a monomer and doesn't dimerize in solution. The fractions containing the pure $V_{HH}$ (as determined by SDS-PAGE) were pooled and the concentration was measured spectrophotometrically. A yield of 5 mg of purified protein per liter of bacterial culture was calculated. The purified protein could be further concentrated by ultrafiltration to 10 mg/ml in PBS or water without any sign of aggregation, as seen on the UV spectrum.

The camel anti-lysozyme $V_{HH}$ affinity measurements

The specificity of the soluble camel $V_{HH}$ for the lysozyme was suggested from the ELISA experiments in which we competed the binding with free antigen. An apparent inhibition constant of around $5.10^{-7}$ and $5.10^{-8}$ M was observed for the α-LYS3 and α-LYS2 respectively. These affinities are consistent with a specific $V_{HH}$-antigen interaction (the polyspecific antibodies generally bind their antigen with affinities of $10^6$ $M^{-1}$ or less (Casali et al. 1989).

Epitope recognition of α-LYS2 and α-LYS3.

To analyse whether the two camel $V_{HH}$ with anti-lysozyme activity bind to the same or to different epitopes we used the techniques of additive binding in ELISA (Friguet et al., 1989). An additivity index of more than 40 indicates pairs of antibodies that can bind simultaneously on the antigen, while additivity indices of less than 20 is characteristic for pairs of antibodies with overlapping epitopes. Our camel α-LYS2 and α-LYS3 had an additivity index of 45. From this experiment it appears that the α-LYS2 and α-LYS3 bind to different epitopes on the lysozyme molecule.

EXAMPLE 3

Making Bivalent Monospecific or Monovalent Bispecific Binding Constructs from Camelid $V_{HH}$'s From the camel $V_{HH}$'s with specificity to tetanus toxin (α-TT1 or α-TT2) or with specificity to lysozyme (α-LYS2 or α-LYS3) cloned in the pHEN4 bacterial expression vector, we made constructs with following characteristics:

1. $V_{HH}$ with ProX repeat. sequences of the camel long hinge including the 3 Cys and part of the CH2 domain. These constructs can be also used as an intermediate for the next constructs.

2. $V_{HH}$ with ProX repeat sequences of the long hinge of camel with one Cys followed by a stopcodon in the pHEN4. These are bivalent constructs with monospecificity.

3. $V_{HH}$ linked with the ProX repeat sequences of the long hinge of camel (without Cys) followed by a second $V_{HH}$. These are monovalent constructs with bispecificity, or bivalent constructs with monospecificity depending on the $V_{HH}$'s.

1. Camel $V_{HH}$ with Camel Long Hinge and Dart of CH2 Domain.

The (pHEN4-α-LYS3) or the (pHEN4-α-TT2) plasmids were digested with BstEII and Xmn I. BstEII cuts in the framework 4 of the camel $V_{HH}$, and Xmn I cuts in the β-lactamase gene of pHEN4. The DNA fragment containing the camel $V_{HH}$ was isolated from agarose gel.

A clone containing a camel $V_{HH}$ with unknown specificity, the camel long hinge and the first part of the CH2 domain cloned in pBluescript (Statagene) was cut with the same enzymes (Bst EII and Xmn I) and the DNA resulting fragment containing the hinge and CH2 parts was isolated from agarose gel.

The two DNA fragments (one containing the $V_{HH}$ of determined specificity, the other containing the coding sequence of the hinge and $CH_2$ domains) were mixed and ligated to each other and used to transform *E. coli* cells. As a result a (pHEN4-α-LYS3-long hinge-CH2) plasmid and a (pHEN4-α-TT2-long hinge-CH2) plasmid have been obtained.

2. Bivalent monospecific constructs (FIGS. 13A, 13B and 15).

The (pHEN4-α-LYS3-long hinge-CH2) plasmid was taken as template for amplification with primers A4 and AM007 (SEQ ID NOS 9 & 10, respectively).

A4 (Sf I site underlined):
5'CATGCCATGACTCGC<u>GGCCCAGCCGG</u>CCATGGCCGA(G,T)GT
(G,C)CAGCT-3'

AM007:
5'GGCCATTTGCGGCCGCATTCCATGGGTTCAGGTTTTGG-3'

These primers anneal respectively with their 3' end to the beginning of the $V_{HH}$ and to the end of the structural upper hinge of the camel long hinge sequence. The primer AM007 will extend the 3' end of the α-LYS3 or of the α-TT2 gene (depending on the template) with (SEQ ID NO: 12) C<u>CCATGG</u>AA<u>TGCGGCCGC</u>AAATGTCC. The NcoI and NotI sites are underlined. These nucleotides up to the Not I site code for the amino acids Pro Met Glu Cys.

The PCR fragment is double digested with Sfi I and Not I, and the resulting fragments are cloned in the pHEN4 vector cleaved with the same enzymes. The ligated material is transformed in WK6 *E. coli* cells and selected on ampicillin. The transformed clones are checked for their insert by PCR and by sequencing. The plasmid (pHEN4-α-LYS3long hinge/Cys) and (pHEN4-α-TT2-long hinge/Cys) were generated.

The extraction of the expressed $V_{HH}$ α-LYS3-long hinge/Cys or α-TT2-long hinge/Cys proteins lead to isolation of a dimerised molecule because of the formation of the disulfide bridge between the Cys residue within the long hinge. Both camel $V_{HH}$ dimer constructs (α-LYS3 long hinge/Cys)$_2$ and α-TT2 long hinge/Cys)$_2$ are well expressed in *E. coli* upon induction with IPTG, and are easily obtained from the periplasm. They were quite soluble and bound the original antigen with high affinity and high specificity.

3. Monovalent bispecific protein constructs (FIGS. 14A, 14B and 16).

In the previous plasmid constructs (pHEN4-α-LYS3long hinge/Cys) and (pHEN4-α-TT2-long hinge/Cys), we have two restriction sites for Nco I. Digestion of the plasmid with this enzyme allows the isolation of the camel $V_{HH}$ gene followed by the long hinge without the Cys codon. Ligation of the (α-LYS3-long hinge) fragment into the pHEN4-α-LYS2 or in the pHEN4-α-TT2 plasmids linearised with NcoI creates the plasmids (pHEN4-α-LYS3-long hinge linker-α-LYS2) or (pHEN4-α-LYS3long hinge linker-α-TT2). Expression of the gene leads to the production of the α-LYS3 $V_{HH}$ linked to the α-LYS2 $V_{HH}$ or linked to the α-TT2 $V_{HH}$ by the intermediate of a linker based on the structural upper hinge of the camel long hinge.

Following this protocol monovalent bispecific proteins consisting of the camel $V_{HH}$ of α-LYS3 linked to the camel $V_{HH}$ of α-LYS2 and that of camel $V_{HH}$ of α-LYS3 linked to the camel $V_{HH}$ of α-TT2 can be isolated. Both proteins are expressed well in *E. coli* and can be extracted from the periplasm. In ELISA the binding properties of the latter protein to the tetanus toxoid and to the lysosyme can be shown.

With these gene constructs at hand it becomes possible and straightforward to exchange either $V_{HH}$ with any other $V_{HH}$ with another specificity.

For example we can exchange the second camel $V_{HH}$ by digesting the plasmid with Pst I, or with Nco I and to ligate the DNA fragment containing the $V_{HH}$-long hinge linker into the pHEN4-$V_{HH}$ linearised with either Pst I or Nco I.

Similarly, we exchanged the first camel $V_{HH}$ α-LYS3 gene from the (pHEN4-α-LYS3long hinge linker-α-LYS2) plasmid construct into (pHEN4-α-TT1-long hinge linker-α-LYS2). This was done by cutting the plasmid with Bst EII and further ligating the DNA fragment containing the (long hinge linker-α-LYS2) into the (pHEN4-α-TT1) plasmid linearised with Bst EII.

With a slight modification of this protocol it becomes even possible to generate multivalent constructs. In this case the ($V_{HH}$-long hinge linker-$V_{HH}$) plasmid needs to be digested with Bst EII and the DNA fragment containing the (long hinge linker-$V_{HH}$) gene should be isolated from agarose gel. Because of the asymmetry in the recognition site of Bst EII, it is only possible to obtain head-to tail ligations upon self ligation. The self-ligated DNA should thereafter (with or without prior size selection) be ligated into the pHEN4-$V_{HH}$ plasmid linearised with Bst EII. This will create a plasmid of the type (pHEN4-[$V_{HH}$-long hinge linker]$_n$).

REFERENCES CITED IN THE PRECEDING EXAMPLES

Borrebaeck et al., (1992) Bio/Technology 10, 697-698.
Casali et al., (1989)Annu. Rev. Immunol. 7, 513-536.

Friguet et al., (1983) J.Immunol. Meth. 60, 351 et (1989) Protein Structure.
A practical approach (Ed. T. E. Creighton) IRL Press p. 287-310)
Glockshuber et al., (1990) Biochemistry 29, 1362-1367.
Hamers-Casterman et al., (1993) Nature 363, 446-448.
Hoogenboom et al., (1991) Nucl. Acids Res. 19, 4133-4137.
Johnson W. C., (1990) Proteins: Structure, Func & Genetics 7, 205-214.
Kabat et a. (1991) Sequences of Proteins of Immunological Interest (US Dept.Health Human Services, Washington) 5th Ed.
Marks et al., (1991) J.Mol.Biol. 222, 581-597.
Montecucco & Schiavo (1993) TIBS 18, 324-329.
Mullinax et al., (1990) Proc.Natl.Acad.Sci USA 87, 8095-8099.
Persson et al., (1991) Proc.Natl.Acad.Sci USA 88, 2432-2436.
Sambrook et al., (1989) Molecular Cloning CSHL Press
Simpson et al., (1990) J. Pharmacol. & Exp. Therap. 254, 98-103.
Skerra and Pluckthun, (1988) Science 240, 1038-1040.

The invention claimed is:

1. A recombinant bivalent monospecific protein comprising two variable fragments ($V_{HH}$) of a heavy chain polypeptide of an immunoglobulin devoid of light chains, linked together with a linker, wherein said variable fragments ($V_{HH}$) have the same antigen binding specificity, wherein said linker is part of a hinge domain of an immunoglobulin devoid of a light chain, wherein said part of a hinge domain is devoid of amino acid residues enabling the dimerization of the $V_{HH}$ fragments, and wherein the amino acid residues enabling the dimerization of the $V_{HH}$ fragments in said hinge are cysteine residues and are deleted.

2. The recombinant bivalent monospecific protein according to claim 1, wherein said hinge domain is the long hinge domain of said immunoglobulin.

3. The recombinant bivalent monospecific protein according to claim 2, wherein said long hinge domain is encoded by a nucleotide sequence comprising nucleotides 400 to 486 of SEQ ID No. 21.

4. The recombinant bivalent monospecific protein according to claim 2, wherein said long hinge domain is encoded by a nucleotide sequence comprising nucleotides 400 to 479 of SEQ ID No. 21.

5. The recombinant bivalent monospecific protein of claim 1, wherein said variable fragments have antigen binding specificity with respect to a bacterial toxin or toxoid selected from the group consisting of toxins produced by Clostridium, Staphylococcus, Pseudomonas, Pasteurella, Yersinia, Bacillus anthracis, Neisseria, Vibrio, enterotoxic E. coli, Salmonella, Shigella, and Listeria.

6. The recombinant bivalent monospecific protein of claim 5, wherein the Clostridium is selected from the group consisting of Clostridium Botulinum and Clostridium Perfringens.

7. The recombinant bivalent mono specific protein of claim 5, wherein the Vibrio is Vibrio cholera.

8. The recombinant bivalent monospecific protein of claim 1, wherein said variable fragments have antigen specificity with respect to a toxin or toxoid selected from the group consisting of toxins produced by anemones, coral, jellyfish, spiders, bees, wasps, scorpions and snakes, including those belonging to the families of Viperidae, Crotalidae, and Lapidea.

9. A pharmaceutical composition, comprising a recombinant bivalent monospecific protein according to claim 1 in admixture with a physiologically acceptable vehicle and/or adjuvant(s).

10. The pharmaceutical composition according to claim 9, wherein the recombinant bivalent monospecific protein passively immunizes against infection or acute intoxication.

11. The pharmaceutical composition according to claim 9, wherein the cause of infection or acute intoxication is selected from the group consisting of Clostridium, Staphylococcus, Pseudomonas, Pasteurella, Yersinia, Bacillus anthracis, *Neisseria, Vibrio*, enterotoxic *E. coli, Salmonella, Shigella*, and *Listeria* bacteria, and anemones, coral, jellyfish, spiders, bees, wasps, scorpions and snakes, including those belonging to the families of Viperidae, Crotalidae, and Lapidea.

12. The pharmaceutical composition of claim 11 wherein the Clostridium is selected from the group consisting of *Clostridium Botulinum* and *Clostridium Perfringens*.

13. The pharmaceutical composition of claim 11, wherein the *Vibrio* is *Vibrio cholera*.

14. A recombinant bivalent monospecific protein comprising two variable fragments ($V_{HH}$) of a heavy chain polypeptide of an immunoglobulin devoid of light chains, linked together with a linker, consisting of a part of a long hinge domain of an immunoglobulin devoid of light chains wherein said part is encoded by a nucleotide sequence that comprises nucleotides 400 to 479 of SEQ ID No. 21 and is devoid of cysteine residues.

15. A recombinant bivalent monospecific protein comprising two variable fragments ($V_{HH}$) of a heavy chain polypeptide of an immunoglobulin devoid of two light chains comprising the amino acid sequence of SEQ ID Nos. 22, 25 or 26, linked together with a linker that is part of a hinge domain of an immunoglobulin devoid of a light chain, wherein said part of a hinge domain is devoid of amino acid residues enabling the dimerization of the $V_{HH}$ fragments, wherein the amino acid residues enabling the dimerization of the $V_{HH}$ fragments in said hinge are cysteine residues and are deleted, and wherein said variable fragments ($V_{HH}$) have the same antigen binding specificity.

16. A recombinant bivalent monospecific protein comprising two variable fragments ($V_{HH}$) of a heavy chain polypeptide of an immunoglobulin devoid of two light chains, linked together with a linker that is part of a hinge domain of an immunoglobulin devoid of a light chain, wherein said part of a hinge domain is devoid of amino acid residues enabling the dimerization of the $V_{HH}$ fragments, wherein the amino acid residues enabling the dimerization of the $V_{HH}$ fragments in said hinge are cysteine residues and are deleted, and, wherein said variable fragments ($V_{HH}$) have the same antigen binding specificity with respect to a bacterial toxin or toxoid selected from the group consisting of toxins produced by *Clostridium, Staphylococcus, Pseudomonas, Pasteurella, Yersinia, Bacillus anthracis, Neisseria, Vibrio*, enterotoxic *E. coli, Salmonella, Shigella*, and *Listeria*.

17. A recombinant bivalent monospecific protein comprising two variable fragments ($V_{HH}$) of a heavy chain polypeptide of an immunoglobulin devoid of two light chains, linked together with a linker that is part of a hinge domain of an immunoglobulin devoid of a light chain, wherein said part of a hinge domain is devoid of amino acid residues enabling the dimerization of the $V_{HH}$ fragments, wherein the amino acid residues enabling the dimerization of the $V_{HH}$ fragments in said hinge are cysteine residues and are deleted, and, wherein said variable fragments ($V_{HH}$) have the same antigen binding specificity with respect to a toxin or toxoid selected from the group consisting of toxins produced by anemones, coral, jellyfish, spiders, bees, wasps, scorpions and snakes including those belonging to the families of Viperidae, Crotalidae, and Lapidea.

18. The recombinant bivalent monospecific protein according to claim 1 comprising at least two variable fragments ($V_{HH}$) of a heavy chain polypeptide of an immunoglobulin devoid of light chains, said variable fragments having the same epitope specificity.

* * * * *

```
                           SEQUENCE LISTING (1) GENERAL INFORMATION:

(iii) NUMBER OF SEQUENCES: 29

(2) INFORMATION FOR SEQ ID NO: 1:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO: 1:

GATGTGCAGC TGCAGGCGTC TGGRGGAGG                                       29

(2) INFORMATION FOR SEQ ID NO: 2:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO: 2:

CGCCATCAAG GTACCGTTGA                                                 20

(2) INFORMATION FOR SEQ ID NO: 3:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO: 3:

CGCCATCAAG GTACCAGTTG A                                               21

(2) INFORMATION FOR SEQ ID NO: 4:

(i) SEQUENCE CHARACTERISTICS:
            (A) LENGTH: 35 base pairs
            (B) TYPE: nucleic acid
            (C) STRANDEDNESS: single
            (D) TOPOLOGY: linear
```

```
    (ii) MOLECULE TYPE: other nucleic acid
         (A) DESCRIPTION: /desc = "oligonucleotide"

(xi) SEQUENCE DESCRIPTION: SEQ ID NO: 4:

CGACTAGTGC GGCCGCGTGA GGAGACGGTG ACCTG                                    35

(2) INFORMATION FOR SEQ ID NO: 5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "oligonucleotide"

(xi) SEQUENCE DESCRIPTION: SEQ ID NO: 5:

TGTCTTGGGT TCTGAGGAGA CGGT                                                24

(2) INFORMATION FOR SEQ ID NO: 6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "oligonucleotide"

(xi) SEQUENCE DESCRIPTION: SEQ ID NO: 6:

TTCATTCGTT CCTGAGGAGA CGGT                                                24

(2) INFORMATION FOR SEQ ID NO: 7:

(i) SEQUENCE CHARACTERISTICS:
        (A) LENGTH: 119 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 7:

Glu Val Gln Leu Gln Ala Ser Gly Gly Gly Ser Val Gln Ala Gly Gly
1               5                   10                  15

Ser Leu Arg Leu Ser Cys Ala Ala Ser Gly Gly Gln Thr Phe Asp Ser
            20                  25                  30

Tyr Ala Met Ala Trp Phe Arg Gln Ala Pro Gly Lys Glu Cys Glu Leu
        35                  40                  45

Val Ser Ser Ile Ile Gly Asp Asp Asn Arg Asn Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asp Arg Leu Asn Pro Glu Asp Thr Ala Val Tyr Tyr Cys
                85                  90                  95

Ala Gln Leu Gly Ser Ala Arg Ser Ala Met Tyr Cys Ala Gly Gln Gly
            100                 105                 110

Thr Gln Val Thr Val Ser Ser
        115

(2) INFORMATION FOR SEQ ID NO: 8:
```

```
        (i) SEQUENCE CHARACTERISTICS:
            (A) LENGTH: 127 amino acids
            (B) TYPE: amino acid
            (C) STRANDEDNESS: <Unknown>
            (D) TOPOLOGY: linear (ii) MOLECULE TYPE: protein (xi) SEQUENCE DESCRIPTION: SEQ ID NO: 8:

Glu Val Gln Leu Gln Ala Ser Gly Gly Gly Ser Val Gln Ala Gly Gly
 1               5                  10                  15

Ser Leu Arg Leu Ser Cys Thr Ala Ala Asn Tyr Ala Phe Asp Ser Lys
            20                  25                  30

Thr Val Gly Trp Phe Arg Gln Val Pro Gly Lys Glu Arg Glu Gly Val
        35                  40                  45

Ala Gly Ile Ser Ser Gly Gly Ser Thr Thr Ala Tyr Ser Asp Ser Val
    50                  55                  60

Lys Gly Arg Tyr Thr Val Ser Leu Glu Asn Ala Lys Asn Thr Val Tyr
 65                  70                  75                  80

Leu Leu Ile Asp Asn Leu Gln Pro Glu Asp Thr Ala Ile Tyr Tyr Cys
                85                  90                  95

Ala Gly Val Ser Gly Trp Arg Gly Arg Gln Trp Leu Leu Leu Ala Glu
            100                 105                 110

Thr Tyr Arg Phe Trp Gly Gln Gly Thr Gln Val Thr Val Ser Ser
        115                 120                 125

(2) INFORMATION FOR SEQ ID NO: 9:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO: 9:

CATGCCATGA CTCGCGGCCC AGCCGGCCAT GGCCGAKGTS CAGCT                           45

(2) INFORMATION FOR SEQ ID NO: 10:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO: 10:

GGCCATTTGC GGCCGCATTC CATGGGTTCA GGTTTTGG                                   38

(2) INFORMATION FOR SEQ ID NO: 11:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"
```

(xi) SEQUENCE DESCRIPTION: SEQ ID NO: 11:

CGCCATCAAG GTACCAGTTG A                                            21

(2) INFORMATION FOR SEQ ID NO: 12:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 12:

CCCATGGAAT GCGGCCGCAA ATGTCC                                       26

(2) INFORMATION FOR SEQ ID NO: 13:

(i) SEQUENCE CHARACTERISTICS:
        (A) LENGTH: 357 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..357

(xi) SEQUENCE DESCRIPTION: SEQ ID NO: 13:

```
GAG GTG CAG CTG CAG GCG TCT GGG GGA GGC TCG GTG CAG GCT GGA GGG     48
Glu Val Gln Leu Gln Ala Ser Gly Gly Gly Ser Val Gln Ala Gly Gly
 1               5                  10                  15

TCT CTG AGA CTC TCC TGT GCG GCC TCT GGG GGA CAG ACC TTC GAT AGT     96
Ser Leu Arg Leu Ser Cys Ala Ala Ser Gly Gly Gln Thr Phe Asp Ser
                20                  25                  30

TAT GCC ATG GCC TGG TTC CGC CAG GCT CCA GGG AAG GAG TGC GAA TTG    144
Tyr Ala Met Ala Trp Phe Arg Gln Ala Pro Gly Lys Glu Cys Glu Leu
                35                  40                  45

GTC TCG AGT ATT ATT GGT GAT GAT AAC AGA AAC TAT GCC GAC TCC GTG    192
Val Ser Ser Ile Ile Gly Asp Asp Asn Arg Asn Tyr Ala Asp Ser Val
     50                  55                  60

AAA GGC CGA TTC ACC ATC TCC CGA GAC AAC GCC AAG AAC ACG GTA TAT    240
Lys Gly Arg Phe Thr Ile Ser Arg Asp Asn Ala Lys Asn Thr Val Tyr
 65                  70                  75                  80

CTG CAA ATG GAC CGT CTG AAT CCT GAG GAC ACG GCC GTG TAT TAC TGT    288
Leu Gln Met Asp Arg Leu Asn Pro Glu Asp Thr Ala Val Tyr Tyr Cys
                85                  90                  95

GCG CAA TTG GGT AGT GCC CGG TCG GCT ATG TAC TGT GCG GGC CAG GGG    336
Ala Gln Leu Gly Ser Ala Arg Ser Ala Met Tyr Cys Ala Gly Gln Gly
                100                 105                 110

ACC CAG GTC ACC GTC TCC TCA                                        357
Thr Gln Val Thr Val Ser Ser
                115
```

(2) INFORMATION FOR SEQ ID NO: 14:

(i) SEQUENCE CHARACTERISTICS:
        (A) LENGTH: 119 amino acids
        (B) TYPE: amino acid
        (D) TOPOLOGY: linear (ii) MOLECULE TYPE: protein (xi) SEQUENCE DESCRIPTION: SEQ ID NO: 14:

```
Glu Val Gln Leu Gln Ala Ser Gly Gly Gly Ser Val Gln Ala Gly Gly
 1               5                  10                  15

Ser Leu Arg Leu Ser Cys Ala Ala Ser Gly Gly Gln Thr Phe Asp Ser
             20                  25                  30

Tyr Ala Met Ala Trp Phe Arg Gln Ala Pro Gly Lys Glu Cys Glu Leu
         35                  40                  45

Val Ser Ser Ile Ile Gly Asp Asp Asn Arg Asn Tyr Ala Asp Ser Val
     50                  55                  60

Lys Gly Arg Phe Thr Ile Ser Arg Asp Asn Ala Lys Asn Thr Val Tyr
 65                  70                  75                  80

Leu Gln Met Asp Arg Leu Asn Pro Glu Asp Thr Ala Val Tyr Tyr Cys
             85                  90                  95

Ala Gln Leu Gly Ser Ala Arg Ser Ala Met Tyr Cys Ala Gly Gln Gly
             100                 105                 110

Thr Gln Val Thr Val Ser Ser
             115
```

(2) INFORMATION FOR SEQ ID NO: 15:

(i) SEQUENCE CHARACTERISTICS:
        (A) LENGTH: 381 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..381

(xi) SEQUENCE DESCRIPTION: SEQ ID NO: 15:

```
GAG GTG CAG CTG CAG GCG TCT GGA GGA GGC TCG GTG CAG GCT GGA GGG      48
Glu Val Gln Leu Gln Ala Ser Gly Gly Gly Ser Val Gln Ala Gly Gly
 1               5                  10                  15

TCT CTG AGG CTC TCT TGT ACA GCC GCT AAT TAC GCC TTT GAT TCC AAG      96
Ser Leu Arg Leu Ser Cys Thr Ala Ala Asn Tyr Ala Phe Asp Ser Lys
             20                  25                  30

ACC GTG GGC TGG TTC CGC CAG GTT CCA GGA AAG GAG CGC GAG GGG GTC     144
Thr Val Gly Trp Phe Arg Gln Val Pro Gly Lys Glu Arg Glu Gly Val
         35                  40                  45

GCG GGT ATC AGT AGT GGT GGC AGT ACC ACA GCC TAT TCC GAC TCC GTG     192
Ala Gly Ile Ser Ser Gly Gly Ser Thr Thr Ala Tyr Ser Asp Ser Val
     50                  55                  60

AAG GGC CGA TAC ACC GTC TCC CTT GAG AAC GCC AAG AAC ACT GTG TAT     240
Lys Gly Arg Tyr Thr Val Ser Leu Glu Asn Ala Lys Asn Thr Val Tyr
 65                  70                  75                  80

CTA CTG ATA GAC AAC CTA CAA CCT GAA GAC ACT GCC ATA TAC TAC TGC     288
Leu Leu Ile Asp Asn Leu Gln Pro Glu Asp Thr Ala Ile Tyr Tyr Cys
             85                  90                  95

GCA GGA GTG AGC GGT TGG CGA GGG CGG CAG TGG CTG CTA CTG GCA GAG     336
Ala Gly Val Ser Gly Trp Arg Gly Arg Gln Trp Leu Leu Leu Ala Glu
             100                 105                 110

ACC TAT CGG TTC TGG GGC CAG GGG ACT CAG GTC ACC GTC TCC TCA         381
Thr Tyr Arg Phe Trp Gly Gln Gly Thr Gln Val Thr Val Ser Ser
             115                 120                 125
```

(2) INFORMATION FOR SEQ ID NO: 16:

(i) SEQUENCE CHARACTERISTICS:

(A) LENGTH: 127 amino acids
        (B) TYPE: amino acid
        (D) TOPOLOGY: linear (ii) MOLECULE TYPE: protein (xi) SEQUENCE DESCRIPTION: SEQ ID NO: 16:

Glu Val Gln Leu Gln Ala Ser Gly Gly Gly Ser Val Gln Ala Gly Gly
 1               5                  10                  15

Ser Leu Arg Leu Ser Cys Thr Ala Ala Asn Tyr Ala Phe Asp Ser Lys
            20                  25                  30

Thr Val Gly Trp Phe Arg Gln Val Pro Gly Lys Glu Arg Glu Gly Val
        35                  40                  45

Ala Gly Ile Ser Ser Gly Gly Ser Thr Thr Ala Tyr Ser Asp Ser Val
    50                  55                  60

Lys Gly Arg Tyr Thr Val Ser Leu Glu Asn Ala Lys Asn Thr Val Tyr
 65                  70                  75                  80

Leu Leu Ile Asp Asn Leu Gln Pro Glu Asp Thr Ala Ile Tyr Tyr Cys
                85                  90                  95

Ala Gly Val Ser Gly Trp Arg Gly Arg Gln Trp Leu Leu Leu Ala Glu
            100                 105                 110

Thr Tyr Arg Phe Trp Gly Gln Gly Thr Gln Val Thr Val Ser Ser
        115                 120                 125

(2) INFORMATION FOR SEQ ID NO: 17:

(i) SEQUENCE CHARACTERISTICS:
        (A) LENGTH: 384 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..384
        (D) OTHER INFORMATION: /product= "Lys2"

(xi) SEQUENCE DESCRIPTION: SEQ ID NO: 17:

GAG GTC CAG CTG CAG GCG TCT GGA GGA GGC TCG GTG CAG GCT GGA CAG      48
Glu Val Gln Leu Gln Ala Ser Gly Gly Gly Ser Val Gln Ala Gly Gln
 1               5                  10                  15

TCT CTG AGA CTC TCC TGT GCG ACC TCT GGA GCC ACC TCC AGT AGC AAC      96
Ser Leu Arg Leu Ser Cys Ala Thr Ser Gly Ala Thr Ser Ser Ser Asn
            20                  25                  30

TGC ATG GGC TGG TTC CGC CAG GCT CCA GGG AAG GAG CGC GAG GGG GTC     144
Cys Met Gly Trp Phe Arg Gln Ala Pro Gly Lys Glu Arg Glu Gly Val
        35                  40                  45

GCA GTT ATT GAT ACT GGT AGA GGG AAT ACA GCC TAT GCC GAC TCC GTG     192
Ala Val Ile Asp Thr Gly Arg Gly Asn Thr Ala Tyr Ala Asp Ser Val
    50                  55                  60

CAG GGC CGA TTG ACC ATC TCC TTA GAC AAC GCC AAG AAC ACG CTA TAT     240
Gln Gly Arg Leu Thr Ile Ser Leu Asp Asn Ala Lys Asn Thr Leu Tyr
 65                  70                  75                  80

CTG CAA ATG AAC AGC CTG AAA CCT GAG GAC ACT GCC ATG TAC TAC TGT     288
Leu Gln Met Asn Ser Leu Lys Pro Glu Asp Thr Ala Met Tyr Tyr Cys
                85                  90                  95

GCA GCA GAT ACA TCC ACT TGG TAT CGT GGT TAC TGC GGA ACA AAT CCA     336
Ala Ala Asp Thr Ser Thr Trp Tyr Arg Gly Tyr Cys Gly Thr Asn Pro
            100                 105                 110

AAT TAC TTT TCG TAC TGG GGC CAG GGG ACC CAG GTC ACC GTC TCC TCA     384

(2) INFORMATION FOR SEQ ID NO: 18:

(i) SEQUENCE CHARACTERISTICS:
        (A) LENGTH: 128 amino acids
        (B) TYPE: amino acid
        (D) TOPOLOGY: linear (ii) MOLECULE TYPE: protein (xi) SEQUENCE DESCRIPTION: SEQ ID NO: 18:

```
Glu Val Gln Leu Gln Ala Ser Gly Gly Gly Ser Val Gln Ala Gly Gln
 1               5                  10                  15

Ser Leu Arg Leu Ser Cys Ala Thr Ser Gly Ala Thr Ser Ser Ser Asn
            20                  25                  30

Cys Met Gly Trp Phe Arg Gln Ala Pro Gly Lys Glu Arg Glu Gly Val
        35                  40                  45

Ala Val Ile Asp Thr Gly Arg Gly Asn Thr Ala Tyr Ala Asp Ser Val
    50                  55                  60

Gln Gly Arg Leu Thr Ile Ser Leu Asp Asn Ala Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Ala Asp Thr Ser Thr Trp Tyr Arg Gly Tyr Cys Gly Thr Asn Pro
            100                 105                 110

Asn Tyr Phe Ser Tyr Trp Gly Gln Gly Thr Gln Val Thr Val Ser Ser
        115                 120                 125
```

(2) INFORMATION FOR SEQ ID NO: 19:

(i) SEQUENCE CHARACTERISTICS:
        (A) LENGTH: 400 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..399
        (D) OTHER INFORMATION: /product= "Lys3"

(xi) SEQUENCE DESCRIPTION: SEQ ID NO: 19:

```
GAT GTG CAG CTG CAG GCG TCT GGA GGA GGC TCG GTG CAG GCT GGA GGG      48
Asp Val Gln Leu Gln Ala Ser Gly Gly Gly Ser Val Gln Ala Gly Gly
 1               5                  10                  15

TCT CTG AGA CTC TCC TGT GCA GCC TCT GGA TAC ACC ATC GGT CCC TAC      96
Ser Leu Arg Leu Ser Cys Ala Ala Ser Gly Tyr Thr Ile Gly Pro Tyr
            20                  25                  30

TGT ATG GGG TGG TTC CGC CAG GCC CCA GGG AAG GAG CGT GAG GGG GTC     144
Cys Met Gly Trp Phe Arg Gln Ala Pro Gly Lys Glu Arg Glu Gly Val
        35                  40                  45

GCA GCA ATT AAT ATG GGT GGT GGT ATC ACC TAC TAC GCC GAC TCC GTG     192
Ala Ala Ile Asn Met Gly Gly Gly Ile Thr Tyr Tyr Ala Asp Ser Val
    50                  55                  60

AAG GGC CGA TTC ACC ATC TCC CAA GAC AAC GCC AAG AAC ACG GTG TAT     240
Lys Gly Arg Phe Thr Ile Ser Gln Asp Asn Ala Lys Asn Thr Val Tyr
65                  70                  75                  80

CTG CTC ATG AAC AGC CTA GAA CCT GAG GAC ACG GCC ATC TAT TAC TGT     288
Leu Leu Met Asn Ser Leu Glu Pro Glu Asp Thr Ala Ile Tyr Tyr Cys
```

```
                   85                  90                  95
GCG GCA GAT TCG ACC ATC TAC GCT AGT TAT TAT GAA TGT GGT CAC GGT         336
Ala Ala Asp Ser Thr Ile Tyr Ala Ser Tyr Tyr Glu Cys Gly His Gly
            100                 105                 110

CTT TCC ACG GGA GGA TAT GGG TAT GAC TCC TGG GGC CAG GGG ACC CAG         384
Leu Ser Thr Gly Gly Tyr Gly Tyr Asp Ser Trp Gly Gln Gly Thr Gln
            115                 120                 125

GTC ACC GTC TCC TCA A                                                   400
Val Thr Val Ser Ser
    130
```

(2) INFORMATION FOR SEQ ID NO: 20:

(i) SEQUENCE CHARACTERISTICS:
        (A) LENGTH: 133 amino acids
        (B) TYPE: amino acid
        (D) TOPOLOGY: linear (ii) MOLECULE TYPE: protein (xi) SEQUENCE DESCRIPTION: SEQ ID NO: 20:

```
Asp Val Gln Leu Gln Ala Ser Gly Gly Gly Ser Val Gln Ala Gly Gly
 1               5                  10                  15

Ser Leu Arg Leu Ser Cys Ala Ala Ser Gly Tyr Thr Ile Gly Pro Tyr
            20                  25                  30

Cys Met Gly Trp Phe Arg Gln Ala Pro Gly Lys Glu Arg Glu Gly Val
        35                  40                  45

Ala Ala Ile Asn Met Gly Gly Gly Ile Thr Tyr Tyr Ala Asp Ser Val
    50                  55                  60

Lys Gly Arg Phe Thr Ile Ser Gln Asp Asn Ala Lys Asn Thr Val Tyr
65                  70                  75                  80

Leu Leu Met Asn Ser Leu Glu Pro Glu Asp Thr Ala Ile Tyr Tyr Cys
                85                  90                  95

Ala Ala Asp Ser Thr Ile Tyr Ala Ser Tyr Tyr Glu Cys Gly His Gly
            100                 105                 110

Leu Ser Thr Gly Gly Tyr Gly Tyr Asp Ser Trp Gly Gln Gly Thr Gln
            115                 120                 125

Val Thr Val Ser Ser
    130
```

(2) INFORMATION FOR SEQ ID NO: 21:

(i) SEQUENCE CHARACTERISTICS:
        (A) LENGTH: 537 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..534

(xi) SEQUENCE DESCRIPTION: SEQ ID NO: 21:

```
GAT GTG CAG CTG CAG GCG TCT GGA GGA GGC TCG GTG CAG GCT GGA GGG         48
Asp Val Gln Leu Gln Ala Ser Gly Gly Gly Ser Val Gln Ala Gly Gly
 1               5                  10                  15

TCT CTG AGA CTC TCC TGT GCA GCC TCT GGA TAC ACC ATC GGT CCC TAC         96
Ser Leu Arg Leu Ser Cys Ala Ala Ser Gly Tyr Thr Ile Gly Pro Tyr
            20                  25                  30

TGT ATG GGG TGG TTC CGC CAG GCC CCA GGG AAG GAG CGT GAG GGG GTC        144
```

```
Cys Met Gly Trp Phe Arg Gln Ala Pro Gly Lys Glu Arg Glu Gly Val
         35                  40                  45

GCA GCA ATT AAT ATG GGT GGT GGT ATC ACC TAC TAC GCC GAC TCC GTG      192
Ala Ala Ile Asn Met Gly Gly Gly Ile Thr Tyr Tyr Ala Asp Ser Val
 50                  55                  60

AAG GGC CGA TTC ACC ATC TCC CAA GAC AAC GCC AAG AAC ACG GTG TAT      240
Lys Gly Arg Phe Thr Ile Ser Gln Asp Asn Ala Lys Asn Thr Val Tyr
 65                  70                  75                  80

CTG CTC ATG AAC AGC CTA GAA CCT GAG GAC ACG GCC ATC TAT TAC TGT      288
Leu Leu Met Asn Ser Leu Glu Pro Glu Asp Thr Ala Ile Tyr Tyr Cys
                 85                  90                  95

GCG GCA GAT TCG ACC ATC TAC GCT AGT TAT TAT GAA TGT GGT CAC GGT      336
Ala Ala Asp Ser Thr Ile Tyr Ala Ser Tyr Tyr Glu Cys Gly His Gly
                100                 105                 110

CTT TCC ACG GGA GGA TAT GGG TAT GAC TCC TGG GGC CAG GGG ACC CAG      384
Leu Ser Thr Gly Gly Tyr Gly Tyr Asp Ser Trp Gly Gln Gly Thr Gln
            115                 120                 125

GTC ACC GTC TCC TCA GAA CCC AAG ATA CCA CAA CCA CAA CCA AAA CCA      432
Val Thr Val Ser Ser Glu Pro Lys Ile Pro Gln Pro Gln Pro Lys Pro
        130                 135                 140

CAA CCA CAA CCA CAA CCA CAG CCA AAA CCA CAA CCA AAA CCT GAA CCC      480
Gln Pro Gln Pro Gln Pro Gln Pro Lys Pro Gln Pro Lys Pro Glu Pro
145                 150                 155                 160

ATG GAA TGC GGC CGC TAC CCG TAC GAC GTT CCG GAC TAC GGT TCC GGC      528
Met Glu Cys Gly Arg Tyr Pro Tyr Asp Val Pro Asp Tyr Gly Ser Gly
                165                 170                 175

CGA GCA TAG                                                          537
Arg Ala (2) INFORMATION FOR SEQ ID NO: 22:

(i) SEQUENCE CHARACTERISTICS:
        (A) LENGTH: 178 amino acids
        (B) TYPE: amino acid
        (D) TOPOLOGY: linear (ii) MOLECULE TYPE: protein (xi) SEQUENCE DESCRIPTION: SEQ ID NO: 22:

Asp Val Gln Leu Gln Ala Ser Gly Gly Gly Ser Val Gln Ala Gly Gly
 1               5                  10                  15

Ser Leu Arg Leu Ser Cys Ala Ala Ser Gly Tyr Thr Ile Gly Pro Tyr
             20                  25                  30

Cys Met Gly Trp Phe Arg Gln Ala Pro Gly Lys Glu Arg Glu Gly Val
         35                  40                  45

Ala Ala Ile Asn Met Gly Gly Gly Ile Thr Tyr Tyr Ala Asp Ser Val
 50                  55                  60

Lys Gly Arg Phe Thr Ile Ser Gln Asp Asn Ala Lys Asn Thr Val Tyr
 65                  70                  75                  80

Leu Leu Met Asn Ser Leu Glu Pro Glu Asp Thr Ala Ile Tyr Tyr Cys
                 85                  90                  95

Ala Ala Asp Ser Thr Ile Tyr Ala Ser Tyr Tyr Glu Cys Gly His Gly
                100                 105                 110

Leu Ser Thr Gly Gly Tyr Gly Tyr Asp Ser Trp Gly Gln Gly Thr Gln
            115                 120                 125

Val Thr Val Ser Ser Glu Pro Lys Ile Pro Gln Pro Gln Pro Lys Pro
        130                 135                 140

Gln Pro Gln Pro Gln Pro Gln Pro Lys Pro Gln Pro Lys Pro Glu Pro
145                 150                 155                 160
```

(2) INFORMATION FOR SEQ ID NO: 23:

(i) SEQUENCE CHARACTERISTICS:
        (A) LENGTH: 912 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..909

(xi) SEQUENCE DESCRIPTION: SEQ ID NO: 23:

```
GAT GTG CAG CTG CAG GCG TCT GGA GGA GGC TCG GTG CAG GCT GGA GGG        48
Asp Val Gln Leu Gln Ala Ser Gly Gly Gly Ser Val Gln Ala Gly Gly
 1               5                  10                  15

TCT CTG AGA CTC TCC TGT GCA GCC TCT GGA TAC ACC ATC GGT CCC TAC        96
Ser Leu Arg Leu Ser Cys Ala Ala Ser Gly Tyr Thr Ile Gly Pro Tyr
             20                  25                  30

TGT ATG GGG TGG TTC CGC CAG GCC CCA GGG AAG GAG CGT GAG GGG GTC       144
Cys Met Gly Trp Phe Arg Gln Ala Pro Gly Lys Glu Arg Glu Gly Val
         35                  40                  45

GCA GCA ATT AAT ATG GGT GGT GGT ATC ACC TAC TAC GCC GAC TCC GTG       192
Ala Ala Ile Asn Met Gly Gly Gly Ile Thr Tyr Tyr Ala Asp Ser Val
     50                  55                  60

AAG GGC CGA TTC ACC ATC TCC CAA GAC AAC GCC AAG AAC ACG GTG TAT       240
Lys Gly Arg Phe Thr Ile Ser Gln Asp Asn Ala Lys Asn Thr Val Tyr
 65                  70                  75                  80

CTG CTC ATG AAC AGC CTA GAA CCT GAG GAC ACG GCC ATC TAT TAC TGT       288
Leu Leu Met Asn Ser Leu Glu Pro Glu Asp Thr Ala Ile Tyr Tyr Cys
                 85                  90                  95

GCG GCA GAT TCG ACC ATC TAC GCT AGT TAT TAT GAA TGT GGT CAC GGT       336
Ala Ala Asp Ser Thr Ile Tyr Ala Ser Tyr Tyr Glu Cys Gly His Gly
            100                 105                 110

CTT TCC ACG GGA GGA TAT GGG TAT GAC TCC TGG GGC CAG GGG ACC CAG       384
Leu Ser Thr Gly Gly Tyr Gly Tyr Asp Ser Trp Gly Gln Gly Thr Gln
        115                 120                 125

GTC ACC GTC TCC TCA GAA CCC AAG ATA CCA CAA CCA CAA CCA AAA CCA       432
Val Thr Val Ser Ser Glu Pro Lys Ile Pro Gln Pro Gln Pro Lys Pro
    130                 135                 140

CAA CCA CAA CCA CAA CCA CAG CCA AAA CCA CAA CCA AAA CCT GAA CCC       480
Gln Pro Gln Pro Gln Pro Gln Pro Lys Pro Gln Pro Lys Pro Glu Pro
145                 150                 155                 160

ATG GCA GAG GTC CAG CTG CAG GCG TCT GGA GGA GGC TCG GTG CAG GCT       528
Met Ala Glu Val Gln Leu Gln Ala Ser Gly Gly Gly Ser Val Gln Ala
                165                 170                 175

GGA CAG TCT CTG AGA CTC TCC TGT GCG ACC TCT GGA GCC ACC TCC AGT       576
Gly Gln Ser Leu Arg Leu Ser Cys Ala Thr Ser Gly Ala Thr Ser Ser
            180                 185                 190

AGC AAC TGC ATG GGC TGG TTC CGC CAG GCT CCA GGG AAG GAG CGC GAG       624
Ser Asn Cys Met Gly Trp Phe Arg Gln Ala Pro Gly Lys Glu Arg Glu
        195                 200                 205

GGG GTC GCA GTT ATT GAT ACT GGT AGA GGG AAT ACA GCC TAT GCC GAC       672
Gly Val Ala Val Ile Asp Thr Gly Arg Gly Asn Thr Ala Tyr Ala Asp
    210                 215                 220
```

Met Glu Cys Gly Arg Tyr Pro Tyr Asp Val Pro Asp Tyr Gly Ser Gly
                165                  170                  175

Arg Ala

```
                                                                -continued

TCC GTG CAG GGC CGA TTG ACC ATC TCC TTA GAC AAC GCC AAG AAC ACG        720
Ser Val Gln Gly Arg Leu Thr Ile Ser Leu Asp Asn Ala Lys Asn Thr
225                 230                 235                 240

CTA TAT CTG CAA ATG AAC AGC CTG AAA CCT GAG GAC ACT GCC ATG TAC        768
Leu Tyr Leu Gln Met Asn Ser Leu Lys Pro Glu Asp Thr Ala Met Tyr
                    245                 250                 255

TAC TGT GCA GCA GAT ACA TCC ACT TGG TAT CGT GGT TAC TGC GGA ACA        816
Tyr Cys Ala Ala Asp Thr Ser Thr Trp Tyr Arg Gly Tyr Cys Gly Thr
                260                 265                 270

AAT CCA AAT TAC TTT TCG TAC TGG GGC CAG GGG ACC CAG GTC ACC GTC        864
Asn Pro Asn Tyr Phe Ser Tyr Trp Gly Gln Gly Thr Gln Val Thr Val
            275                 280                 285

TCC AGC GGC CGC TAC GAC GTT CCG GAC TAC GGT TCC GGC CGA GCA            909
Ser Ser Gly Arg Tyr Asp Val Pro Asp Tyr Gly Ser Gly Arg Ala
        290                 295                 300

TAG                                                                    912
```

(2) INFORMATION FOR SEQ ID NO: 24:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO: 24:

```
Asp Val Gln Leu Gln Ala Ser Gly Gly Gly Ser Val Gln Ala Gly Gly
1               5                   10                  15

Ser Leu Arg Leu Ser Cys Ala Ala Ser Gly Tyr Thr Ile Gly Pro Tyr
            20                  25                  30

Cys Met Gly Trp Phe Arg Gln Ala Pro Gly Lys Glu Arg Glu Gly Val
        35                  40                  45

Ala Ala Ile Asn Met Gly Gly Gly Ile Thr Tyr Tyr Ala Asp Ser Val
    50                  55                  60

Lys Gly Arg Phe Thr Ile Ser Gln Asp Asn Ala Lys Asn Thr Val Tyr
65                  70                  75                  80

Leu Leu Met Asn Ser Leu Glu Pro Glu Asp Thr Ala Ile Tyr Tyr Cys
                85                  90                  95

Ala Ala Asp Ser Thr Ile Tyr Ala Ser Tyr Tyr Glu Cys Gly His Gly
            100                 105                 110

Leu Ser Thr Gly Gly Tyr Gly Tyr Asp Ser Trp Gly Gln Gly Thr Gln
        115                 120                 125

Val Thr Val Ser Ser Glu Pro Lys Ile Pro Gln Pro Gln Pro Lys Pro
    130                 135                 140

Gln Pro Gln Pro Gln Pro Gln Pro Lys Pro Gln Pro Lys Pro Glu Pro
145                 150                 155                 160

Met Ala Glu Val Gln Leu Gln Ala Ser Gly Gly Ser Val Gln Ala
                165                 170                 175

Gly Gln Ser Leu Arg Leu Ser Cys Ala Thr Ser Gly Ala Thr Ser Ser
            180                 185                 190

Ser Asn Cys Met Gly Trp Phe Arg Gln Ala Pro Gly Lys Glu Arg Glu
        195                 200                 205

Gly Val Ala Val Ile Asp Thr Gly Arg Gly Asn Thr Ala Tyr Ala Asp
    210                 215                 220

Ser Val Gln Gly Arg Leu Thr Ile Ser Leu Asp Asn Ala Lys Asn Thr
225                 230                 235                 240
```

-continued

```
Leu Tyr Leu Gln Met Asn Ser Leu Lys Pro Glu Asp Thr Ala Met Tyr
                245                 250                 255
Tyr Cys Ala Ala Asp Thr Ser Thr Trp Tyr Arg Gly Tyr Cys Gly Thr
            260                 265                 270
Asn Pro Asn Tyr Phe Ser Tyr Trp Gly Gln Gly Thr Gln Val Thr Val
        275                 280                 285
Ser Ser Gly Arg Tyr Asp Val Pro Asp Tyr Gly Ser Gly Arg Ala
290                 295                 300
```

(2) INFORMATION FOR SEQ ID NO: 25:

(i) SEQUENCE CHARACTERISTICS:
        (A) LENGTH: 86 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 25:

```
Xaa Val Gln Leu Gln Ala Ser Gly Gly Gly Ser Val Gln Ala Gly Xaa
1               5                   10                  15
Ser Leu Arg Leu Ser Cys Ala Xaa Ser Gly Xaa Trp Xaa Arg Gln Ala
            20                  25                  30
Pro Gly Lys Glu Xaa Glu Xaa Val Xaa Xaa Arg Xaa Thr Ile Ser Xaa
        35                  40                  45
Asp Asn Ala Lys Asn Thr Xaa Tyr Leu Xaa Met Asn Ser Leu Xaa Pro
    50                  55                  60
Glu Asp Thr Ala Xaa Tyr Tyr Cys Ala Ala Xaa Trp Gly Gln Gly Thr
65                  70                  75                  80
Gln Val Thr Val Ser Ser
                85
```

(2) INFORMATION FOR SEQ ID NO: 26:

(i) SEQUENCE CHARACTERISTICS:
        (A) LENGTH: 87 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 26:

```
Xaa Val Gln Leu Gln Ala Ser Gly Gly Gly Ser Val Gln Ala Gly Xaa
1               5                   10                  15
Ser Leu Arg Leu Ser Cys Ala Xaa Ser Gly Xaa Xaa Trp Xaa Arg Gln
            20                  25                  30
Ala Pro Gly Lys Glu Xaa Glu Xaa Val Xaa Xaa Arg Xaa Thr Ile Ser
        35                  40                  45
Xaa Asp Asn Ala Lys Asn Thr Xaa Tyr Leu Xaa Met Asn Ser Leu Xaa
    50                  55                  60
Pro Glu Asp Thr Ala Xaa Tyr Tyr Cys Ala Ala Xaa Trp Gly Gln Gly
65                  70                  75                  80
Thr Gln Val Thr Val Ser Ser
                85
```

(2) INFORMATION FOR SEQ ID NO: 27:

(i) SEQUENCE CHARACTERISTICS:
        (A) LENGTH: 120 base pairs

-continued

```
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO: 27:

GCGGCCCAGC CGGCCATGGC CCAGCTGCAG CTGCAGGACC TCGAGGATCC GGTCACCGTC        60

TCCAGCGGCC GCTACCCGTA CGACGTTCCG GACTACGGTT CCGGCCGAGC ATAGACTGTT       120

(2) INFORMATION FOR SEQ ID NO: 28:

(i) SEQUENCE CHARACTERISTICS:
            (A) LENGTH: 6 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 28:

Ile Gln Val Gln Leu Gln
1               5

(2) INFORMATION FOR SEQ ID NO: 29:

(i) SEQUENCE CHARACTERISTICS:
            (A) LENGTH: 5 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 29:

Val Thr Val Ser Ser
1               5
```